(12) United States Patent
Roberts, II

(10) Patent No.: US 6,620,800 B1
(45) Date of Patent: Sep. 16, 2003

(54) METHODS AND COMPOSITIONS TO ASSESS OXIDATIVE BRAIN INJURY

(75) Inventor: L. Jackson Roberts, II, Gallatin, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/342,813

(22) Filed: Jun. 29, 1999

Related U.S. Application Data

(60) Provisional application No. 60/091,136, filed on Jun. 29, 1998.

(51) Int. Cl.$^7$ ............................ A01N 57/00; A61K 31/66
(52) U.S. Cl. ........................ 514/115; 514/117; 514/119
(58) Field of Search ....................... 435/1; 514/1, 125, 514/183, 214, 762, 772.3, 116, 117, 119, 215

(56) References Cited

PUBLICATIONS

L J Roberts II et al., Jounal of Biological Chemistry, "Formation of Isoprostane–like Compounds (Neuroprostanes) in Vivo from Docosahexaenoic Acid," 1998, vol. 273, No. 22, pp. 13605–13612.*

TM Devlin, Biochemistry with Clinical Correlations, 3rd ed. (Wiley–Liss, Inc., 1992), pp. 586–591.*

Merriam Webster Online, Encyclopedia Britannica 2001, "metabolie".*

Ahlskog J, Utti R, Low P, Tyce G, Nickander K, Petersen R, and Kokmen E. No evidence for systemic oxidant stress in Parkinson's or Alzheimer's disease. Movement Disorders 1995; 10:566–73.

Atsom, J., Sweetman, B.J., Baertschi, S.W., Harris, T.M., and Roberts, L.J. (1990) *Biochemistry* 29, 3760–3765.

Braak H and Braak E. Beuropathological standing of Alzheimer–related changes. Acta Neuropathol 1991; 82–239–59.

Bui, T., and Straus, D.S. (1998) Biochem. *Biophys. Acta.* 1397, 31–42.

Conner, W.E., Neuringer, N., and Reisbick, S. (1992) *Nutri Rev.* 50, 21–29.

Forman, B.M., Tontonoz, P., Chen, J., Brun, R.P., Spiegelman, B..M., and Evans, R.M. (1995) *Cell* 83, 803–812.

Fukushima, J. (1992) *Prostaglandins Leukotrienes Essent. Fatty Acids* 47, 1–12.

Fukushima, M. (1990) *Eicosanoids* 3, 189–199.

Honn, K.V., and Marnett, L.J. (1985) *Biochem. Biophys. Res. Commun.* 129, 34–40.

Jonsson, H.T., Middleditch, B.S., Schexnayder, M.A., and Desiderio, D.M. (1976) *J. Lipid. Res.* 17, 1–6.

Khachaturian, Z.S. Diagnosis of Alzheimer's disease. (1985) *Arch. Neurol.* 42, 1097–1105.

Kim, I.–K., Lee, J.–H., Sohn, H.–W. Kim, H.–S., and Kim, S.–H. (1993) *FEBBS Lett.*. 321, 209–214.

Kliewer, S.A., Lenhard, J.M., Willson, T.M., Patel, I., Morris, D.C., and Lehmann, J.M. (1995) *Cell* 83, 813–819.

Knight, J.A. (1997) *Ann. Clin. Lab. Sci.* 27, 11–25.

Longmire, A.W., Swift, L.L., Roberts, L.J., II, Awad, J.A., Burk, R.F., and Morrow, J.D. (1994) *Biochem. Pharmacol.* 47, 1173–1177.

Mahley RW. Apolipoprotein E: cholesterol transport protein with expanding role in cell biology. Science 1988; 240: 622–630.

Markesbery, W.R. (1997) *Free Radic. Biol. Med.* 23, 134–147.

Melegos, D.M., Diamandis, E.P., Oda, H., Urade, Y., and Hayaishi, O. (1996) *Clin. Chem.* 42, 1984–1991.

Middledtich, B.S., (1975) *Prostaglandins* 9, 409–411.

Mirra, S.S., Heyman, A., McKeel, D., Sumi, S.M., Crain, B.J., Brownlee, L.M., Vogel, F.S., Hughes, J.P., van Belle, G., and Berg, L. The Consortium to Establish a Registry for Alzheimer's Disease (CERAD). Part II. Standardization of the neuropathologic assessment of Alzheimer's disease. (1991) *Neurology* 41, 479–486.

Montine, T.J., Montine, K.S., and Swift, L.L. Central nervous system lipoproteins in Alzheimer's disease (1997) *Am. J. Pathol.* 151, 1571–1575.

Moore, S.A., Yoder, E., Murphy, S., Dutton, G.R., and Spector, A.A. (1991) *J. Neurochem.* 56, 518–524.

Morrow, J.D., and Roberts, L.J. II The isprostanes: unique bioactive products of lipic peroxidation. (1997) *Prog. Lipid Res.* 36, 1–21.

Morrow, J.D., Awad, J.A., Boss, H.J., Blair, I.A., and Roberts, L.J., II (1992) *Proc. Natl. Acad, Sci, U.S.A.* 89, 10721–10725.

Morrow, J.D., Awad, J.A., Wu, A., Zackert, W.E., Daniel, V.C., and Roberts, L.J., II (1996) *J. Biol. Chem.* 271, 23185–23190.

Morrow, J.D., Harris, T.M., and Roberts, L.J., II (1990) *Anal. Biochem.* 184, 1–10.

Narumiya, S., Ohno, K., Fujiwara, M., and Fukushima, M. (1986) *J. Pharmacol. Exp. Ther.* 239, 506–511.

Narumiya, S., Ohno, K., Fukushima, M., and Fujiwara, M. (1987) *J. Pharmacol. Exp. Ther.* 242, 306–311.

(List continued on next page.)

*Primary Examiner*—Scott D. Priebe
*Assistant Examiner*—Joseph Woitach
(74) *Attorney, Agent, or Firm*—Kohn & Associates, PLLC

(57) ABSTRACT

A method to assess oxidative stress in vivo includes the steps of measuring an amount of neuroprostanes in a biological sample before the ex vivo development of neuroprostanes in a sample, comparing the measured amount of neuroprostanes with a control and assessing oxidative stress in vivo based on this comparison. There is also provided a marker for oxidated stress by an increase of neuroprostanes in a biological sample compared to a control sample. A diagnostic tool for determining the presence of a neurodegenerative disease provides for determining an increased amount of neuroprostanes in a biological sample compared to that of a control sample.

5 Claims, 23 Drawing Sheets

OTHER PUBLICATIONS

Roberts, L.J., II, and Morrow, J.D. (1997) *Biochim. Biophys. Acta.* 1345–121–135.

Salem, N., Jr., and Niebylske, C.D. (1995) *Mol. Membr. Biol.* 12, 131–134.

Shahabi, N.A., Chegini, N., and Wittliff, J.L. (1987) *Exp. Cell Biol.* 55, 18–27.

Simonian, N.a., and Coyle, J.T. (1996) *Annu. Rev. Pharmacol. Toxicol.* 36, 83–106.

Skinner, E.R. Watt, C., Besson, J.A. O., and Best, P.V. (1993)*Brain* 116, 717–725.

Taber, D.F., Morrow, J.D., and Roberts, L.J., II (1997) *Prostaglandins* 53, 63–67.

Tokugawa, Y., Kunishige, I., Kubota, Y., Shimoya, K., Nobunaga, T., Kimura, T., Saji, F., Murata, Y., Eguchi, N., Oda, H., Urade, Y., and Hayaishi, O. (1998) *Biol Reprod.* 58, 600–607.

* cited by examiner

METHODS AND COMPOSITIONS TO ASSESS OXIDATIVE BRAIN INJURY

CROSS-REFERENCE TO RELATED APPLICATIONS

This application is a conversion of U.S. Provisional Application Ser. No. 60/091,136, filed Jun. 29, 1998, which is incorporated herein by reference.

GOVERNMENT SUPPORT

National Institute of Health GM 42057.

BACKGROUND OF THE INVENTION

1. Field of the Invention

This invention relates to a method of assessing oxidative stress-in vivo by quantification of markers and their metabolites formed by free radical mediated oxidation.

2. Description of Related Art

Free radicals derived primarily from oxygen have been implicated in the pathophysiology of a number of human diseases, such as atherosclerosis, ischemia-reperfusion injury, inflammatory diseases, cancer and aging. A variety of methods have been developed to assess oxidative stress; however, some of these methods have limited sensitivity or specificity, while others are either too invasive or not adaptable for human investigation. Halliwell, B., et al. The Measurement Of Free Radical Reactions In Humans: Some Thoughts For Future Experimentation. *FEBS Letters.* 213:9–14, 1987.

Unfortunately, oxidative stress is difficult to assess in humans due to lack of reliable methods to assess oxidant stress in vivo. As one author stated, "one of the greatest needs in the field now is the availability of a non-invasive test to probe the is oxidative stress status of humans." Id.

Regional increases in oxidative damage are a feature of brain tissue obtained post mortem from patients with Alzheimer's disease (reviewed in Markesbery, W. R., 1997). However, an objective index of oxidative damage associated with AD that may be assessed during life is lacking. Such a biomarker could have an important impact on the ability to test hypotheses concerning oxidative damage in AD patients by permitting repeated evaluation to follow progression of disease and to quantify response to experimental therapeutic interventions.

Lipid peroxidation is a prominent manifestation of oxidative challenge in brain (reviewed in Markesbery, WR, 1997). Recently, it has been shown that markers of lipid peroxidation are increased in cerebrospinal fluid (CSF) of AD patients compared to control subjects (Lovell et al, 1997; Montine et al., 1997). Although these studies suggest that quantification of lipid peroxidation products in CSF may provide an intra vitam index of oxidative damage to brain, the assays employed have shortcomings, including the need for large volumes of CSF and measuring highly reactive molecules, such as 4-hydroxynonenal, that limit their interpretation or widespread application.

Previously, a series of prostaglandin $F_2$-like compounds, termed $F_2$-isoprostanes ($F_2$-IsoPs), were disclosed that are produced by free radical-catalyzed peroxidation of arachidonic acid independent of the cyclooxygenase enzyme (Morrow et al., 1990). Significant advantages to quantifying $F_2$-IsoP as an index of oxidative stress are their specificity for lipid peroxidation, their chemical stability, and the relatively small tissue volumes required for their detection.

Free radicals are generally short lived and thus, indirect methods of detection are required. Pryor, W., On The Detection Of Lipid Hydroperoxides In Biological Samples, FREE RADICAL BIOLOGY & MEDICINE, Vol. 7, pages 177–178, 1989. Standard detection methods include: electron spin resonance (directly), electron spin resonance (spin trapping), thiobarbituric acid reactive substances (TBARS), detection of malonaldehyde by direct methods (such as HPLC of malonaldehyde itself or as its dinitrophenylhydrazone), detection of other oxidation products from polyunsaturated fatty acids (such as 4-hydroxynonenal), measurement of lipid hydroperoxides, detection of volatile hydrocarbons (ethane, pentane and ethylene), detection of oxidation products from lipids other than polyunsaturated fatty acids (e.g., cholesterol), oxidation of methional, methionine, or 2-keto-4-thiomethylbutanoic acid to ethylene, oxidation of benzoic acid to carbon dioxide (often with radiolabelled carbon dioxide), oxidation of phenol benzoic acid, or aspirin to hydroxylated products, determination of decreases in antioxidant levels (e.g., decreased GSH, tocopherol, or ascorbate) or of increases in the oxidized products from antioxidants (e.g., tocopherol quinone or the ascorbyl radical), detection of oxidized DNA bases (e.g., thymine glycol, 8-hydroxydeoxyguanosine), detection of oxidized products from proteins (e.g., methionine sulfoxide from methionine) or of proteins oxidized to carbonyl-containing products that then react with hydride-reducing agents, detection of adducts of DNA bases (e.g., by enzymatic hydrolysis post-labeling using P32), and chemiluminescence methods. Id.

Also, docosahexaenoic acid (C22:6ω3)(DHA) has been the subject of considerable interest owing to the fact that it is highly enriched in the brain, particularly in gray matter, where it comprises approximately 25–35% of the total fatty acids in aminophospholipids (Salem et al., 1986; Skinner et al., 1993). Although DHA is present in high concentrations in neurons, neurons are incapable of elongating and desaturating essential fatty acids to form DRA. Rather, DHA is synthesized primarily by astrocytes after which it is secreted and taken up by neurons (Moore et al., 1991). Although the precise function of DHA in the brain is not well understood, deficiency of DHA is associated with abnormalities in brain function (Conner et al., 1992). Applicants considered the possibility that IsoP-like compounds could be formed by free radical-induced peroxidation of DHA. Because such compounds would be two carbons longer in length than IsoPs, it would be inappropriate to term these compounds IsoPs. Since DHA is highly enriched in neurons in the brain, applicants therefore propose to term these compounds "neuroprostanes" (NPs).

It would therefore be useful to develop additional methods for assessing oxidative stress in vivo which are neither too invasive nor limited to animal models.

SUMMARY OF THE INVENTION

According to the present invention, there is provided a method of assessing oxidative stress in vivo by measuring an amount of neuroprostanes in a biological sample before the ex vivo development of neuroprostanes in a sample, comparing the measured amount of neuroprostanes with a control and assessing oxidative stress in vivo based on this comparison. There is also provided a marker for oxidative stress by the increase of neuroprostanes in a biological sample compared to a control sample. A diagnostic tool for determining the presence of a neurodegenerative disease determines an increased amount of neuroprostanes in a biological sample compared to that of a control sample.

DESCRIPTION OF THE DRAWINGS

Other advantages of the present invention will be readily appreciated as the same becomes better understood by reference to the following detailed description when considered in connection with the accompanying drawings wherein.

DETAILED DESCRIPTION OF THE INVENTION

Figure 1:
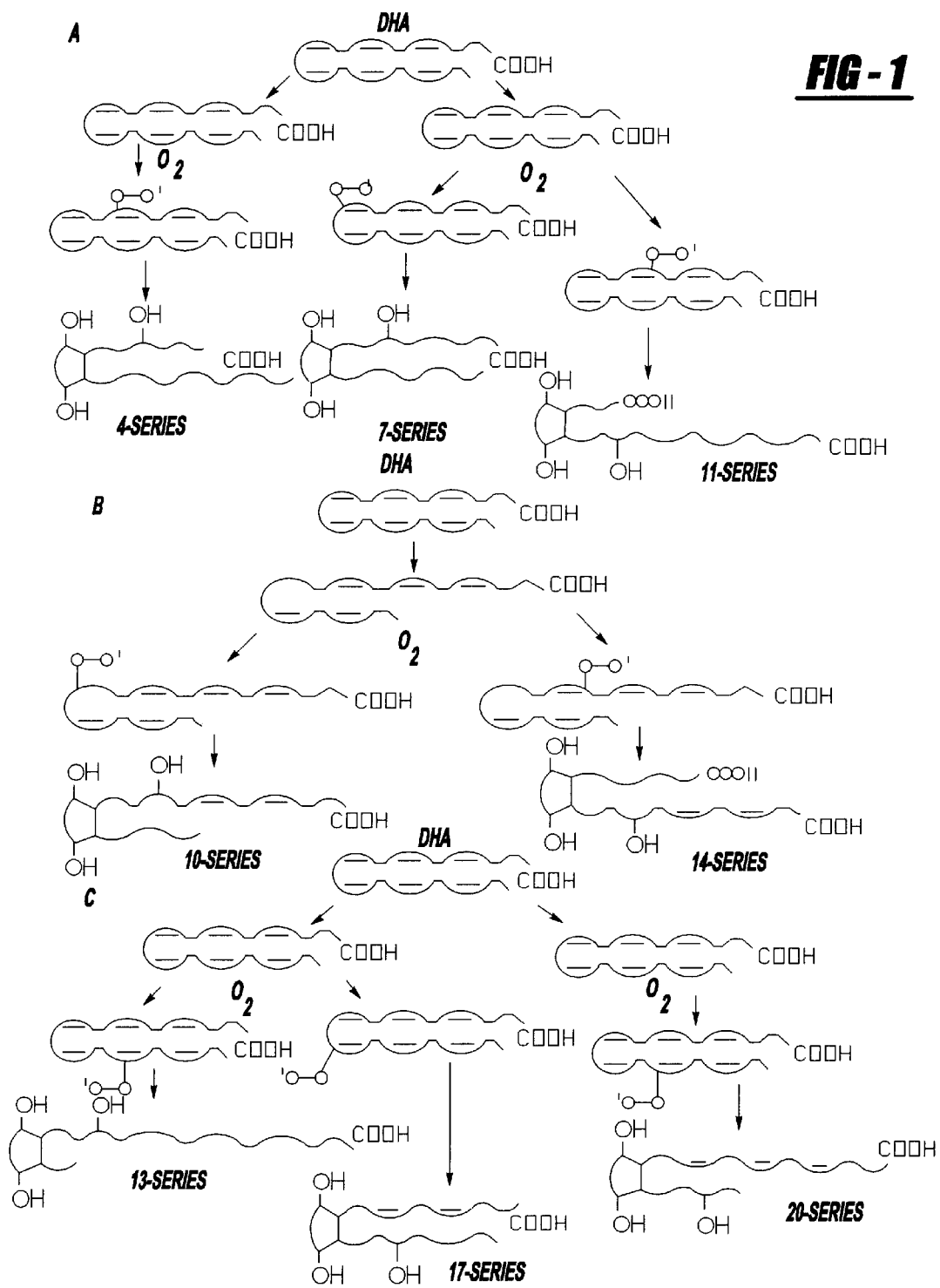
FIG. 1 is a diagram showing the pathway for the formation of $F_4$-NPs by nonenzymatic peroxidation of DHA (A–C)

Generally, the present invention provides a method of assessing oxidative stress in vivo by measuring the amount of a neuroprostane in a biological sample before the ex vivo development of neuroprostanes in a sample, then comparing the measured amount of neuroprostanes with the control sample and assessing oxidative stress in vivo based on the comparison. There is also provided a marker for oxidative stress based on the increase of neuroprostanes in a biological sample compared to that of a control sample.

Isoprostanes (IsoPs), and metabolites thereof, are prostaglandin (PG)-like compounds that are formed nonenzymatically in vivo by free radical-induced peroxidation of arachidonic acid (AA). Their formation proceeds through bicyclic endoperoxide $PGH_2$-like intermediates. The endoperoxide intermediates are reduced to form $PGF_2$-like compounds ($F_2$-IsoPs) (Morrow et al., 1990) or undergo rearrangement to form E-ring and D-ring compounds($E_2/D_2$-IsoPs) (Morrow et al., 1994) and thromboxane-like compounds (isothromboxanes) (Morrow et al., 1996). A novel aspect of the formation of IsoPs is that, unlike cyclooxygenase-derived prostaglandins, IsoPs are formed in situ esterified to phospholipids and subsequently released (Morrow, et al., 1992). Quantification of $F_2$-IsoPs has emerged as one of the most accurate approaches to assess oxidant injury in vivo (Roberts, et al., 1997; Morrow et al, 1997; Moore et al., 1998). Furthermore, IsoPs are capable of exerting potent biological activity (Roberts et al., 1997; Morrow et al, 1997).

Cyclopentenone (CP)[1] prostaglandins (PG) of the A and J series have been shown to be produced in vitro by dehydration of the cyclopentane ring of $PGE_2$ and $PGD_2$, respectively These compounds have attracted considerable attention because they exert unique biological actions. CP-PGs are actively incorporated into cells and accumulate in the nucleus (Narumiya et al., 1986); Narumiya et al., 1987). They have been shown to inhibit cellular proliferation with a $G_1$ cell cycle arrest and to induce differentiation, an effect that may be related to their ability to modulate a variety of growth-related and stress-induced genes (Fukushima, 1992; Fukushima, 1990; Bui et al, 1998). These cytostatic effects can be reversible, but higher concentrations are cytotoxic and induce apoptosis (Fukushima 1990; Kim et al, 1993; Fukushima et al., 1989). Interestingly, at very low concentrations, PGA was found to stimulate cellular proliferation (Shahabi et al., 1987). CP-PGs can also activate nuclear peroxisome proliferator-activated receptor-γ and suppress macrophage activation and inflammatory responses (Forman et al, 1995; Kliewer, 1995; Ricote et al. 1998). Furthermore, CP-PGs exhibit antiviral activity (Santoro, 1997). The common feature in these compounds is the presence of a reactive α,β-unsaturated carbonyl group, which is very susceptible to nucleophilic addition reactions and seems to be essential for many of their biological effects (Boyland et al., 1968; Atsmon et al., 1990; Honn, et al. 1985).

Although the biological effects exerted by CP-PGs have been studied in some detail, the extent to which they are formed in vivo has been the subject of continuing controversy for over two decades (Attalah et al., 1974; Middledtich, 1975; Jonsson, et al., 1976). Fueling this controversy has always been the uncertainty as to what extent dehydration of $PGE_2$ and $PGD_2$ ex vivo during sample processing contributes to the amount of $PGA_2$ and $PGJ_2$ detected. Recently, $\Delta^{12}$-$PGJ_2$ was definitely identified in human urine by Hayaishi and co-workers (Hirata et al., 1988). However, the amounts in urine from males were >2-fold higher than the amounts in urine from females. This is difficult to reconcile with the evidence suggesting that there is no sexual difference in the amount of $PGD_2$ produced in vivo in humans (Morrow et al. 1991). Convincing evidence was presented that the $\Delta^{12}$-$PGJ_2$ detected in urine unlikely arose as a result of dehydration of urinary $PGD_2$ ex vivo during sample processing. However, it is difficult to know to what extent $PGD_2$ may undergo dehydration in the genitourinary tract prior to voiding. This is of particular interest since the same authors recently reported that high levels of PGD synthase are present in human male reproductive organs and that seminal plasma greatly facilitates dehydration of $PGD_2$ (Tokugawa et al., 1998). Furthermore, they also recently reported that the level of PGD synthase in male urine is approximately twice that found in female urine (Melegos et al., 1996). Taken together, these findings suggest that at least some of the $\Delta^{12}$-$PGJ_2$ detected in urine may have arisen from dehydration of $PGD_2$ in the genitourinary tract and may explain the higher levels of $\Delta^{12}$-$PGJ_2$ in urine from males. This does not confute the occurrence of $\Delta^{12}$-$PGJ_2$ in human urine, but only raises the question of its origin, that being whether it arose from systemic sources or from local production in the genitourinary tract. Therefore, it still remains unclear whether CP-PGs are ubiquitously produced throughout the body.

Table 3 shows a comparison of the relative amounts of $A_4/J_4$-neuroproteins formed with that of $E_4/D_4$-neuroprostanes formed during oxidation of rat brain in vitro, both of which are readily detectable following oxidation of the brain.

|  | Mean (ng/g tissue) | SEM |
|---|---|---|
| Normal brain $E_4/D_4$-NPs | 11.8 | 0.7 |
| Oxidized brain $E_4/D_4$-NPs | 446.3 | 81.5 |
| Normal brain $A_4/J_4$-NPs | 0 | — |
| Oxidized brain $A_4/J_4$-NPs | 98.5 | 32.6 |

Iso thromboxane-like compounds are formed by oxidation of arachidonic acid (Morrow et al, *J. of Bio. Chem.*, Vol. 271, No. 38, 1996). Accordingly, similar compounds with a thromboxane ring should be formed by oxidation of decosahexaenoic acid.

Figure 23:
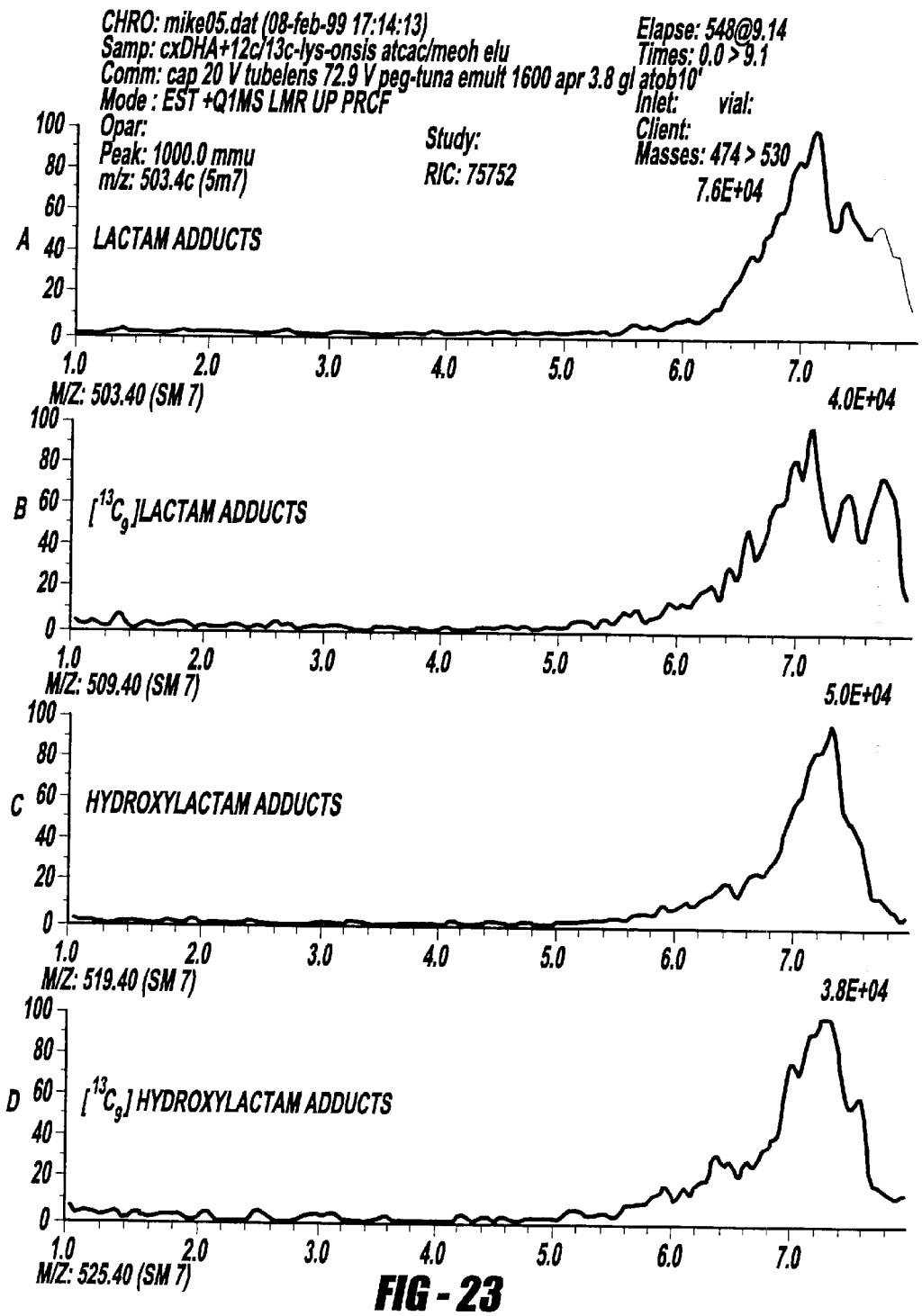
FIGS. 23A–D shows a liquid chromatography electrospray mass spectrometry for (a) lactam adducts formed with lysine; (b) hydroxylactam adducts formed with lysine; (c) lactom adducts formed with $[^{13}C_6]$ lysine; and (d) hydroxylactam adducts for med with $[^{13}C_6]$ lysine.

Isolevuglandin-like compounds are also produced from the oxidation of docosahexaenoic acid. These compounds readily adduct to lysine, forming lactam and hydroxylactam adducts. Experiments were performed in which docosahexaenoic acid was oxidized in the presence of a mixture of lysine and [$^{13}C_6$] labeled lysine. This was then analyzed for lactam and hydrolactam adducts by liquid chromatography electrospray mass spectrometry. The lactam adducts formed with lysine have a mass to charge ratio of 503 and the hydroxylactam adducts have a mass to charge ratio of 519. The respective lactam and hydroxylactam adducts formed with [$^{13}C_6$] lysine have mass to charge ratios of 509 and 525, respectively, as can be seen in FIG. 23.

One of the interests is that IsoP-like compounds can be formed from DHA which derives from the fact that a role for free radicals in the pathogenesis of a number of neuordegenerative diseases, e.g. Alzheimer's disease, Parkinson's disease, Huntington's disease, and amyotrophic lateral sclerosis, has been suggested (Simonian et al., 1996; Knight, 1997; Markesbery, 1997. Thus, quantification of such compounds provides a unique marker and diagnostic tool of oxidative injury in the brain. Furthermore, these compounds, like IsoPs, exert biological activity. This is supported by the finding that $PGF_{4\alpha}$, the four series F-prostaglandin corresponding to the structure expected from cyclooxygenase action on C22:6, is approximately equipotent with cyclooxygenase-derived $PGF_{2\alpha}$ in contracting gerbil colonic smooth muscle strips (Markesbery, 1997). In addition, the formation of NPs esterified in lipids has significant effects on the biophysical properties of neuronal membranes, which impairs normal neuronal function. This is particularly relevant, since it has been suggested that one of the physiological functions of DHA is to maintain a certain state of membrane fluidity and promote interactions with membrane proteins that are optimum for neuronal function (Salem, 1995; Dratz, 1986).

The mechanism by which $F_4$-NPs could be formed is outlined in FIG. 1, A–C. As noted, five DHA radicals are initially generated, which following addition of molecular oxygen, results in the formation of eight peroxyl radicals. These peroxyl radicals then undergo endocyclization followed by further addition of molecular oxygen to form eight bicyclic endoperoxide intermediate regioisomers, which are then reduced to form eight F-ring NP regioisomers. Each regioisomer is theoretically comprised of eight racemic diastereomers for a total of 128 compounds. A nomenclature system for the IsoPs has been established and approved by the Eicosanoid Nomenclature Committee in which the different regioisomer classes are designated by the carbon number on which the side chain hydroxyl is located with the carboxyl carbon designated as C-1 (Attalah et al., 1974). Thus, in accordance with this nomenclature system, the F-ring NP regioisomers are similarly designated as 4-series $F_4$-NPs, 7-series $F_4$-NPs, etc.

Compounds were analyzed employing gas chromatography (GC) mass spectrometry (MS) Levels. of putative $D_4E_4$-NPs increased dramatically 380-fold after oxidation from 15.2±6.3 ng/mg DHA to 5773±1024 ng/mg DHA (n=3). Subsequently, a variety of chemical methods and liquid chromatography tandem MS definitely identified these compounds as $D_4E_4$-NPs. The formation of $D_4E_4$-NPs was explored from a biological source, rat brain synaptosomes. Basal levels of $D_4E_4$-NPs were 3.78±0.6 ng/mg protein and increased 54-fold after oxidation (n=4). These compounds were detected in fresh brain tissue from rats at a level of 12.1±2.4 ng/g brain tissue (n=3). Thus, these studies have identified novel D/E-ring IsoP-like compounds derived from DHA. They are readily detectable in brain tissue in vivo suggesting that ongoing oxidative stress is present in the central nervous system of normal animals, and presumably humans. Identification of these compounds provides a rationale to examine their role in neurological disorders associated with oxidant stress.

Additionally, these neuroprostanes which are formed by the oxidation of docosehexaenoic acid are susceptible to further oxidation. This susceptibility results from the additional 1,4 diene double bonds on the side chains of the compounds. It is important to note that the D-, E-, A-, and J-ring structures, thromboxane ring structure and the isolevuglandins-like structure will all react in the same manner and the side chain ring structure can also be comprised of any of the ring structure.

Also provided by the present invention are metabolites of all the neuroprostanes and isothromboxane-like compounds. These compounds are metabolized by processes of beta oxidation, omega oxidation, double bond reduction, dehydrogenation of the side chain hydroxyl groups and in the case of $E_4$, $D_4$-and $A_4/J_4$-neuroprostanes reduction of the ring carbonyl to a hydroxyl group. It was also discovered that polar glutathione conjugates and their derivatives of $A_2/J_2$-isoprostanes also occur and thus such conjugates should also be formed from $A_4/J_4$-neuroprostanes.

The above discussion provides a factual basis for the use of neuroprostanes as diagnostic tools for assessing oxidative stress. The methods used with and the utility of the present invention can be shown by the following non-limiting examples and accompanying figures.

EXAMPLES

General Methods

Experimental Procedures

Materials—Docosahexaenoic acid, pentafluorobenzyl bromide, and disopropylethylamine were purchased from Sigma; dimethylformamide, undecane, and 1-butaneboronic acid from Aldrich; N,O-bis(tri-methylsilyl) triflucroacetamide from Supelco (Bellefone, Pa.); [$^2H_9$] N,O-bis (trimethysilyl) trifluoroacetamide from Regis Chemical (Morton Grove, Ill.);.organic solvents from Baxter Healthcare (Burdick and Jackson-Brand, McGaw Park, Ill.); C-18 Sep-Paks from Waters Associates (Milford, Mass.); 60ALK6D TLC plates from Whatman (Maidstone, UK.); and [$^2H_4$]$PGF_{2\alpha}$ from Cayman Chemical (Ann Arbor, Mich.).

Oxidation of DEA-DHA and AA were oxidized in vitro using iron/ADP/ascorbate as described (Longmire et al, 1994).

Purification and Analysis of $F_4$-NPs—Free and esterified $F_4$ were extracted using a C-18 Sep-Pak cartridge, converted to a pentafluorobenzyl ester, purified by TLC, converted to a trimethylsilyl ether derivative, and quantified by stable isotope dilution negative ion chemical ionization gas chromatography mass spectrometry using [$^2H_4$]$PGF_{2\alpha}$ as an internal standard using a modification of the method described for the quantification of $F_2$-IsoPs (Morrow et al, 1994). Instead of scraping 1 cm below to 1 cm above where $PGF_{2\alpha}$ methyl ester migrates on TLC for analysis of $F_2$-IsoPsI the area scraped was extended to 3 cm above where $PGF_{2\alpha}$ methyl ester migrates. This extended area of the TLC plate was determined to contain $F_4$-NPs by analyzing small 5-mm cuts using approaches for their identification described below The M—.$CH_2C_6F_5$ ions were monitored for quantification (m/z 593 for $F_4$-NPs and m/z 573 for [$^2H_4$]PGF$_{2\alpha}$). Quantification of the total amount of $F_4$-NPs and $F_2$-IsoPs was determined by integrating peak areas. Formation of cyclic boronate derivatives and hydrogenation were performed as described (Morrow et al. 1990). Electron ionization mass spectra were obtained using a Finnigan Incos 50B quadropole instrument as described (Morrow et al., 1994).

Analysis of $F_4$-NPs in Human Cerebrospinal Fluid—Cerebrospinal fluid was obtained from seven subjects following informed consent. Subjects with Alzheimer's disease (n=4) had been diagnosed with probable Alzheimer's disease during life. Control subjects (n=3) were age-matched individuals without clinical evidence of dementia or other neurological disease; each had annual neuropsychological testing with all test scores within the normal range. Ventricular cerebrospinal fluid was collected as part of a rapid autopsy protocol. Mean post-mortem intervals were 2.9±0.3 h in control subjects and 2.±0.2 h in Alzheimer's patients. Brains were evaluated using standard criteria for Alzheimer's disease (Khachaturian 1985; Mirra et al, 1991). Patients with brainstem or cortical Lewy body formation, or significant cerebrovascular disease, were excluded. Control subjects demonstrated only age-associated alterations. Statistical analysis of data was performed using the unpaired t test.

Molecular Modeling of NP-containing Phosphatidylserine—Molecular modeling was performed with Macspartan computer software.

Results

Figure 2:
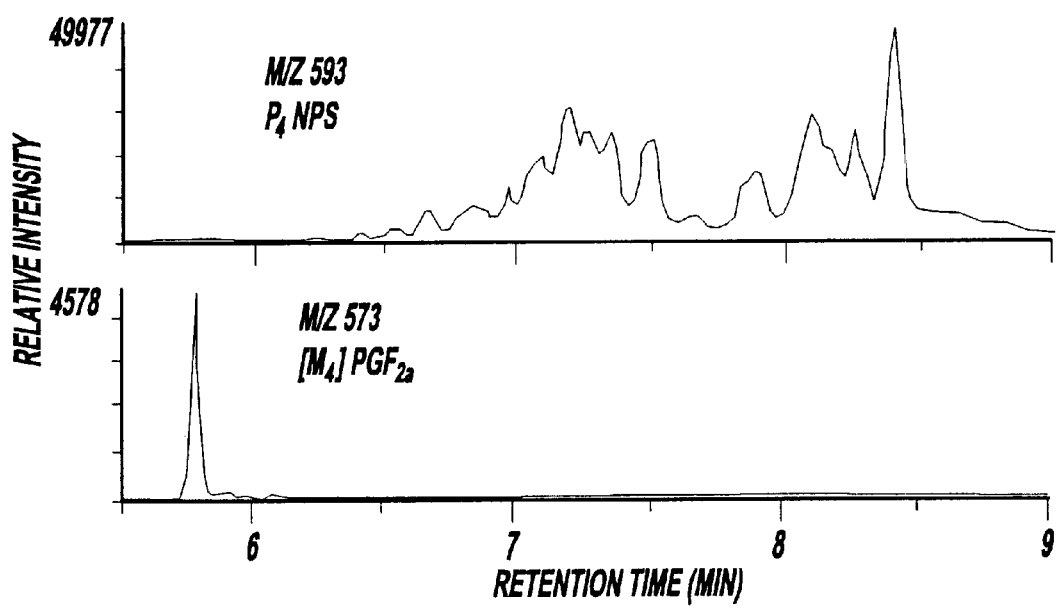
FIG. 2 is a selected ion current chromatograms obtained from the analysis of $F_4$-NPs generated during iron/ADP/ascorbate-induced oxidation of DHA in vitro; The series of peaks in the m/z 593 ion current chromatogram represent putative $F_4$-NPs, and the single peak in the m/z 573 ion current chromatogram represents the $[^2H_4]$ $PGF_{2\alpha}$ internal standard.

A representative selected ion current chromatogram obtained from the analysis for $F_4$-NPs following oxidation of DHA in vitro with iron/ADP/ascorbate is shown in FIG. 2. A series of m/z 593 peaks eluted over approximately a 90 second period beginning approximately 30 seconds after the elution of the [$^2H_4$]PGF$_{2\alpha}$ internal standard. $F_4$-NPs would be expected to have a longer GC retention time than PGF$_{2\alpha}$ because their C-value is two units higher. The time scales of some of the chromatograms obtained from the analysis of $F_4$-NPs shown in subsequent figures are compressed or expanded compared with that in FIG. 2; this may give the impression that the relative abundances/pattern of the different isomers detected differs. Furthermore, the retention times over which the $F_4$-NPs elute may differ somewhat in the different figures, because these analyses were performed on different days using different columns that vary somewhat in length.

Figure 3:
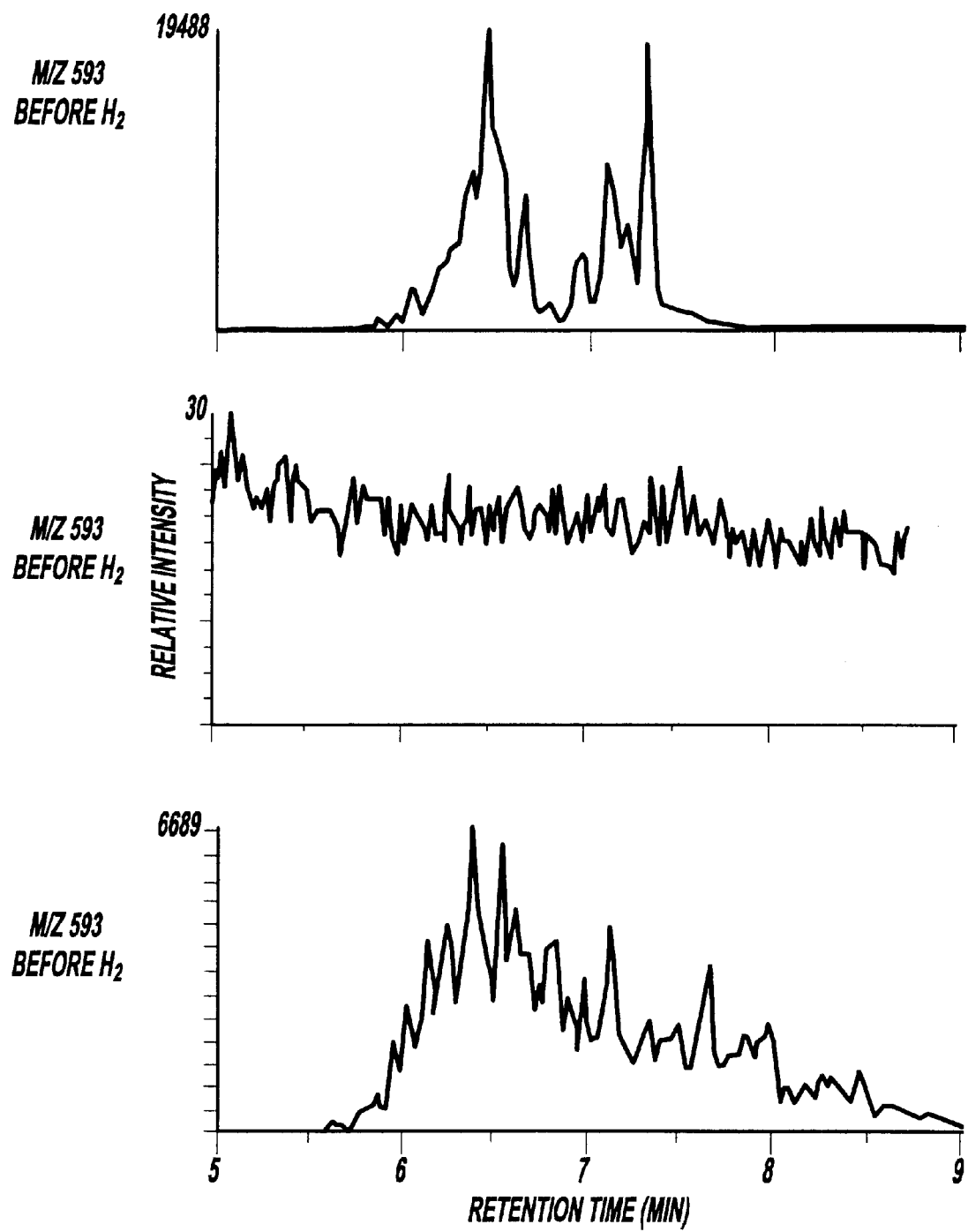
FIG. 3 is a chromatogram showing an analysis of putative $F_4$-NPs before and after catalytic hydrogenation, "in the absence of hydrogenation, intense peaks are present in the m/z 593 ion current chromatogram representing $F_4$-NPs and absent are peaks of significant intensity eight atomic mass units higher at m/z 601. Following catalytic hydrogenation, intense peaks appear at m/z 601; indicating that the m/z 593 compounds have four double bonds.

Analysis of these compounds as a [$^2H_9$ trimethylsilyl ether derivative resulted in a shift in the m/z 593 peaks to m/z 620, indicating the presence of three hydroxyl groups (not shown) Analysis following catalytic hydrogenation is shown in FIG. 3. Prior to hydrogenation, no peaks were present eight Da above m/z 593 at m/z 601. However, following hydrogenation, intense peaks appear at m/z 601, indicating the presence of four double bonds. The pattern of the hydrogenated compounds differs significantly from that of the nonhydrogenated compounds, because hydrogenation converts the compounds into new compounds that are resolved differently than the nonhydrogenated compounds.

Figure 4:
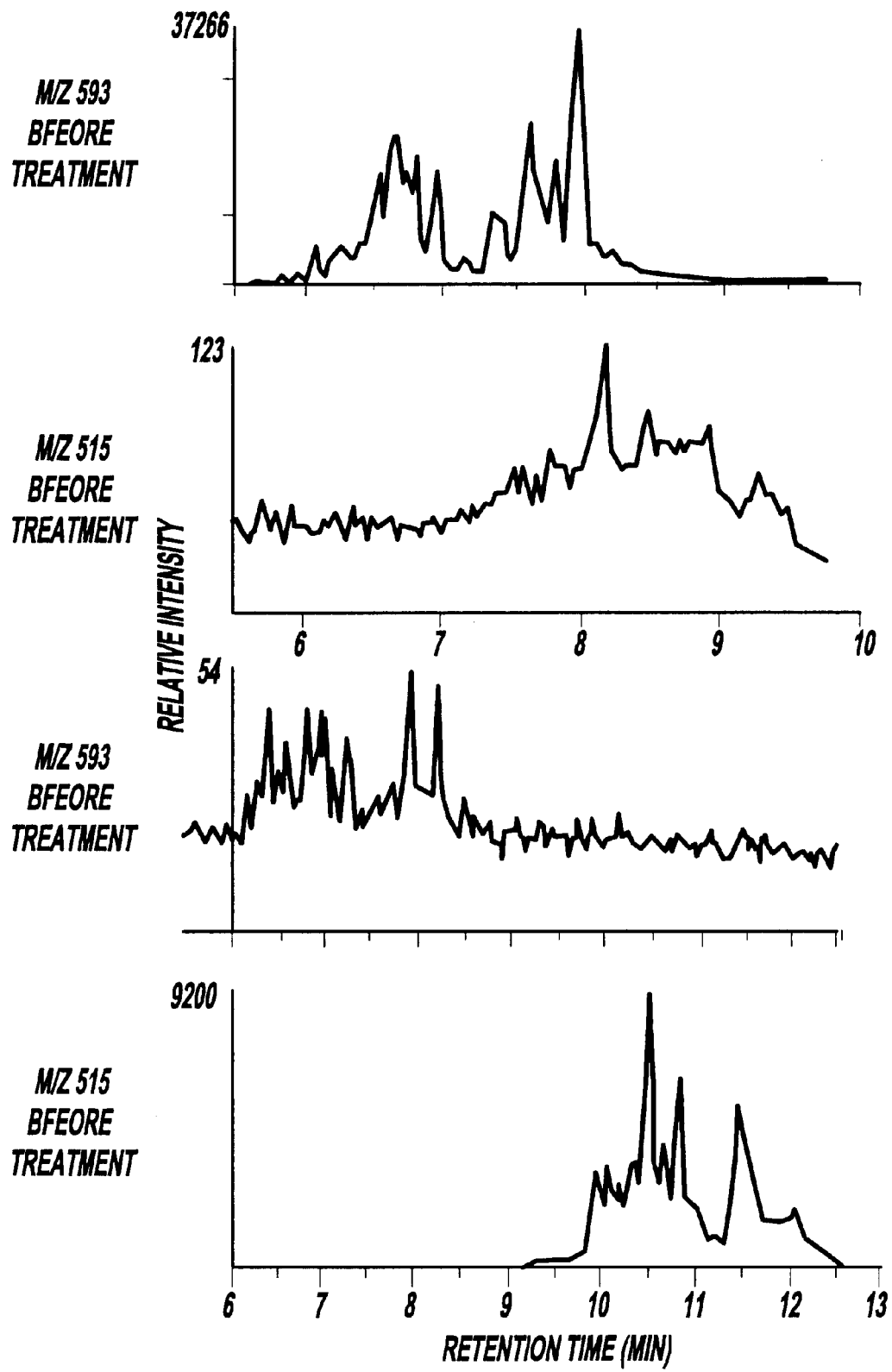
FIG. 4 is a chromatogram showing the formation of a cyclic butylboronate derivative of putative $F_4$-NPs; The $M-CH_2C_6F_5$ ion for the pentafluorobenzyl ester, cyclic butylboronate, trimethylsilyl ether derivative is m/z 515, in the absence of treatment of the compounds with 1-butaneboronic acid, the peaks representing the putative $F_4$-NPs are present in the m/z 593 ion current chromatogram, and no peaks of significant intensity are present in the m/z 515 ion current chromatogram, however, analysis of compounds treated with 1-butaneboronic acid revealed a disappearance of the m/z 593 peaks and the appearance of intense peaks at m/z 515.

$F_4$-NPs are formed by reduction of endoperoxide intermediates (FIG. 1). Thus, the cyclopentane ring hydroxyls must be oriented cis, but they can be either $\alpha,\alpha$ or $\beta,\beta$. Evidence that these compounds contained a cyclopentane (prostane) ring with cis-oriented hydroxyls was obtained by analyzing the compounds as a cyclic boronate derivative (FIG. 4). PGF$_2$ compounds with cis-oriented prostane ring hydroxyls will form a cyclic boronate derivative bridging the ring hydroxyls (Pace-Asiak et al, 1971). The M—CH$_2$C$_6$F$_5$ ion for the cyclic boronate derivative is m/z 515. When the compounds were analyzed as a pentafluorobenzyl ester, trimethysilyl ether derivative, no intense peaks were present at m/z 515. However, when the pentafluorobenzyl ester derivatives were treated with 1-butaneboronic acid and then converted to a trimethylsilyl ether derivative, the intense peaks at m/z 593 were no longer present and intense peaks appeared at m/z 515. Again, the pattern of the m/z 515 peaks differs from that of compounds that were not treated with 1-butaneboronic acid because of differences in resolution of the individual compounds as a cyclic boronate derivative.

Figure 5:
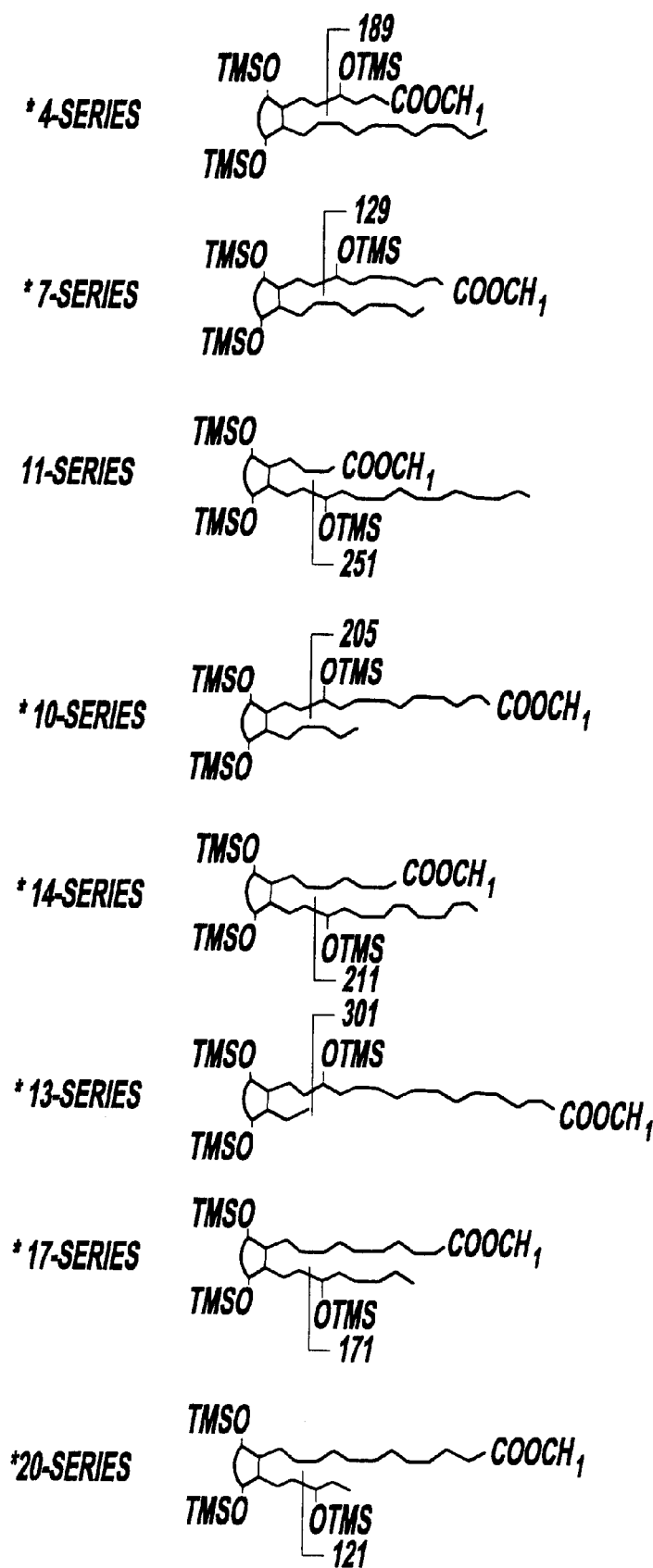
FIG. 5 is a diagram showing the predicted specific α-cleavage ions of the trimethylsiloxy substituents on the side chains of the different $F_4$-NP regioisomer series; The α-cleavage ions for the regioisomer series designated by asterisks were prominent ions in the mass spectrum shown in FIG. 6.
Figure 6:
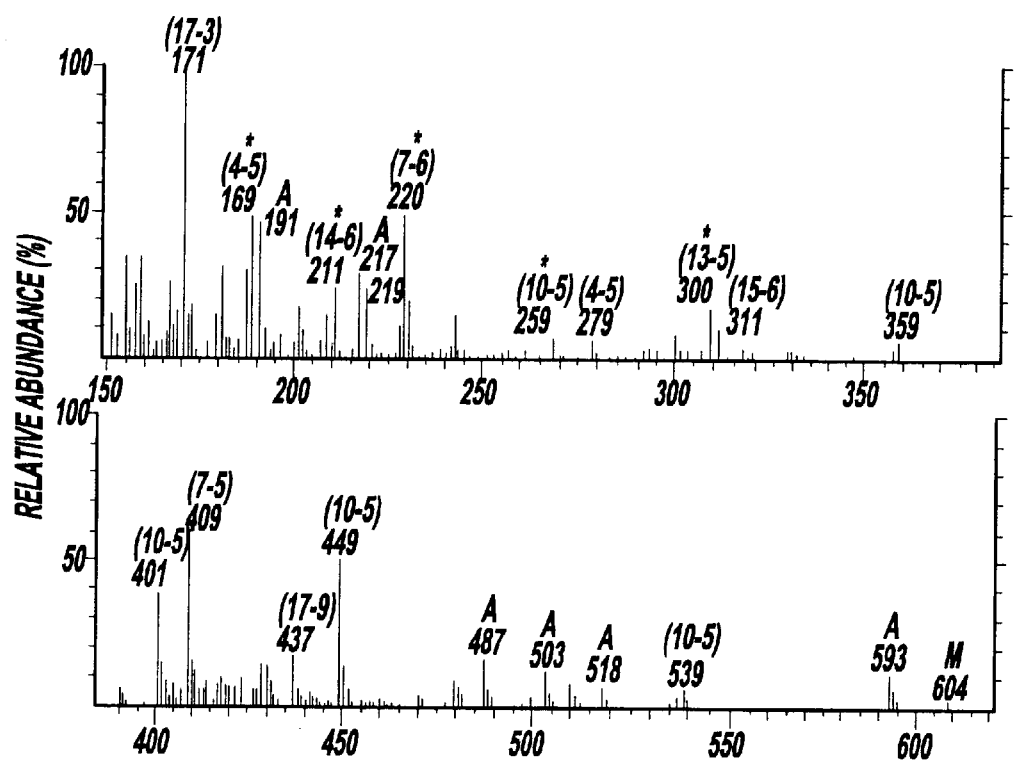
FIG. 6 is an electron ionization mass spectrum obtained of putative $F_4$-NPs as a methyl ester, trimethylsilyl ether derivative; An intense molecular ion is present at m/z 608, the ions designated with an "A" are common ions generated from all regioisomers; The designations (17-S), (4-S), etc. indicate ions specifically generated by compounds in the 17-series, 4-series regioisomers, etc; ions further designated with an asterisk being specific α-cleavage ions of the trimethylsiloxy substituents for the different regioisomer classes as indicated in FIG. 5.

Finally, these compounds were subjected to analysis by electron ionization mass spectrometry as a methyl. ester, trimethylsilyl ether derivative. Multiple mass spectra consistent with compounds representing the different regioisomers of $F_4$-NPs eluted from the GC column over approximately 45 seconds. This elution time differs from that of the pentafluorobenzyl ester derivatives used for negative ion chemical ionization, because methyl esters elute from the GC column much earlier and thus the duration over which they elute is compressed. When analyzed by electron impact mass spectrometry, the different $F_4$-NP regioisomers would be expected to give characteristic $\alpha$-cleavage ions of the trimethylsiloxy substituents on the side chains (FIG. 5). One of the mass spectra obtained is shown in FIG. 6. The ions designated with "A" are ions that would be generated from all of the different regioisomers. These include, in addition to the molecular ion at m/z 608, m/z-593 (M−15, loss of .CH$_3$) m/z 539 (M−90, loss of Me$_3$SiOH), m/z 518 (M−2× 90)), m/z 501 (M−(90+15)), m/z 487 (M−121, loss of .OCH$_3$+90), m/z 217 (Me$_3$SiO—CH=CH=O$^+$SiMe$_3$), a characteristic ion of F-ring prostanoids (Pace-Acsiak, 1989), and m/z 191 (Me$_3$SiO$^+$==CH—OSiMe$_3$), a rearrangement ion characteristic of F-ring prostanoids (Pace-Asciak, 1989). The ions designated (17-S), (4-S), etc. indicate ions generated specifically from 17-series, 4-series, etc. regioisomers. These include the following: (a) 10-series regioisomer ions mlz 539, (M−69, loss CH$_2$(CH$_2$)$_2$CH$_3$), m/z 449 (M−(69+ 2×90)), (b) 17-series regioisomer ion m/z 43.7 (M−171, loss of .CH(Me$_3$SiOH)CH$_2$CH=CHCH$_2$CH$_3$), (c) 7-series regioisomer ion m/z 409 (M−(109+90), loss of .CH$_2$CH=CHCH$_2$CH=CHCH$_2$CH$_3$+90), (d) 13-series regioisomer ions m/z 401 (M−207, loss of .CH$_2$CH=CHCH$_2$CH=CHCH$_2$CH=CH(CH$_2$)$_2$ COOCH$_3$), m/z 311, (M−(207+90)), m/z 219 (M−(309+90), loss of .CH (Me$_3$SiOH)CH$_2$CH=CHCH$_2$CH=CHCH$_2$ CH=CH(CH$_2$)$_2$CO OCH$_3$+90), and (e) 4-series regioisomer ion m/z 279 [M−(149+2×90), loss of .CH$_2$CH= CHCH$_2$CH=CHCH$_2$CH=CHCH$_2$CH$_3$+2×90). The six ions further designated with an asterisk represent specific $\alpha$-cleavage ions of the trimethylsiloxy substituents of different regioiosomers as shown in FIG. 5. These data indicated that this was a mass spectrum of a mixture of six of the eight regioiosomers co-eluting simultaneously from the GC column. This evidence for the presence of predicted six out of eight regioiosomers supports the proposed mechanism of formation of these compounds outlined in FIG. 1.

Figure 7:
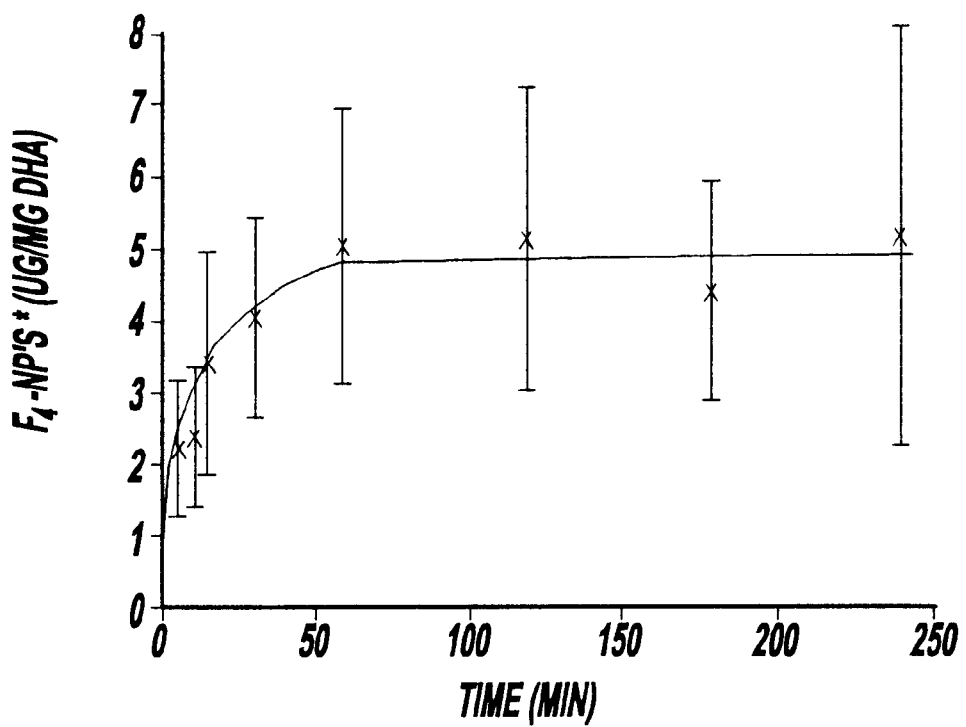
FIG. 7 is a graph showing time-course of formation of $F_4$-NPs during oxidation of DHA in vitro by iron/ADP/ascorbate.
Figure 8:
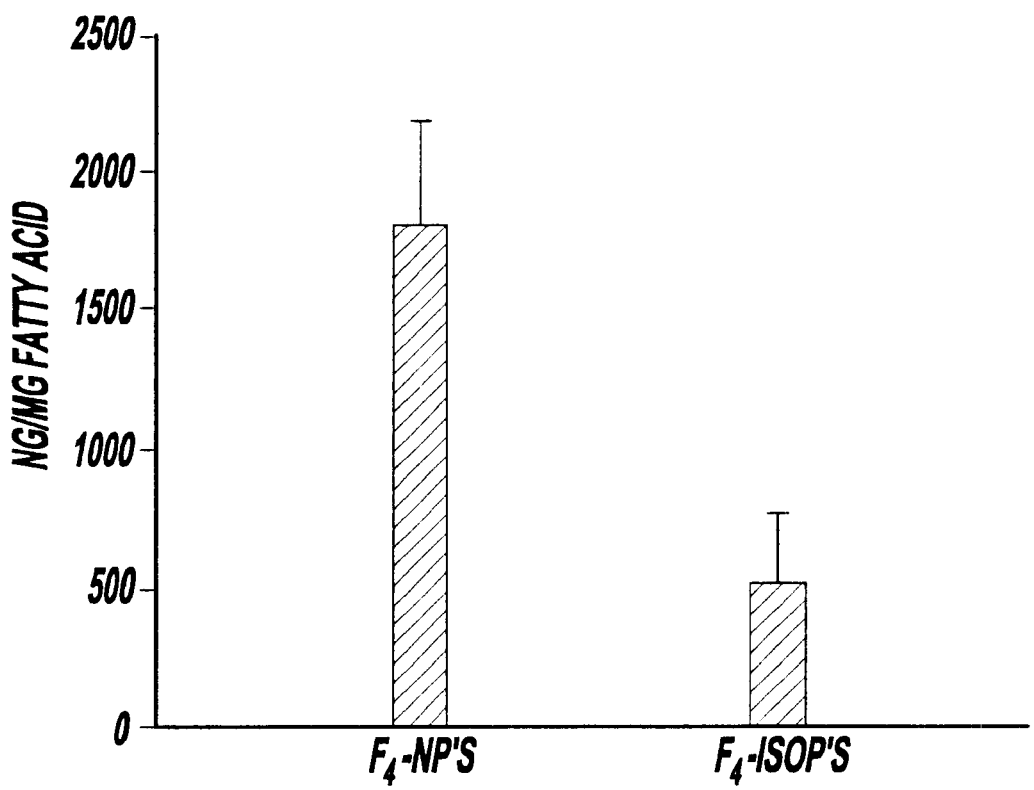
FIG. 8 is a graph showing relative amounts of $F_4$-NPs and $F_2$-IsoPs formed during co-oxidation of equal amounts of DHA and AA in vitro.

The time course of formation of $F_4$-NPs during oxidation of DHA using iron/ADP/ascorbate was rapid, reaching a maximum level of approximately 5 $\mu$g/mg DHA at 50 minutes (FIG. 7). The amounts of $F_2$-IsoPs formed from oxidation of AA were compared with the amounts of $F_4$-NPs formed from DHA. In these experiments, equal molar amounts of AA and DHA were co-oxidized with Fe/ADP/ascorbate and the total amounts of $F_2$-IsoPs and $F_4$-NPs generated quantified. Interestingly, the relative amounts of $F_4$-NPs formed exceeded that of $F_2$-IsoPs by a mean of 3.4-fold (FIG. 8).

Figure 9:
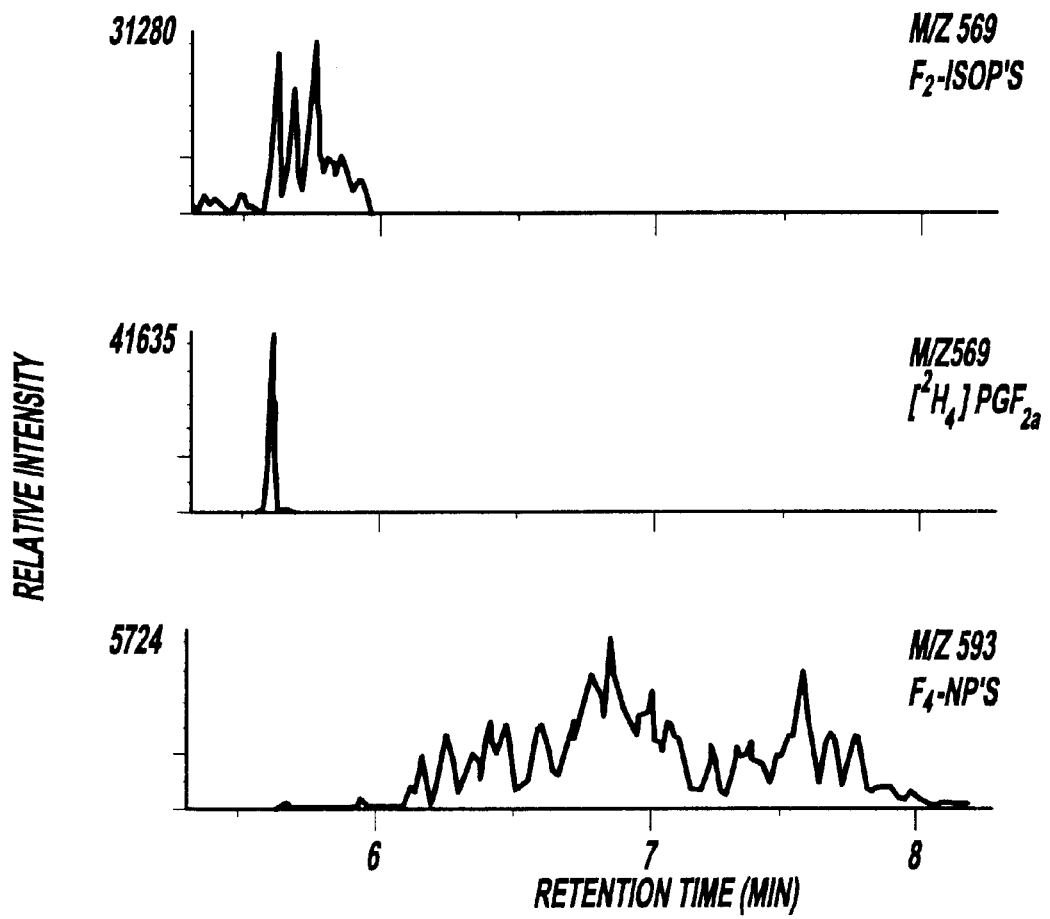
FIG. 9 is a selected ion current chromatogram obtained from the analysis for $F_2$-IsoPs and $F_4$-NPs esterified in whole rat brain; The peaks in the m/z 569 ion current chromatogram represent $F_2$-IsoPs; the peak in the m/z 573 ion current chromatogram is $[^2H_4]PGF_{2\alpha}$; the peaks in the m/z 593 ion current chromatogram represent $F_4$-NPs; the total amounts of $F_2$-IsoPs and $F_4$-NPs present were 7,9 and 6.3 ng/g brain tissue, respectively.

Experiments were undertaken to determine whether $F_4$-NPs are present esterified in brain lipids in vivo (Table I). Both $F_2$-IsoPs and $F_4$-NPs were present at readily detectable levels esterified in lipids of normal whole rat brain at levels of 10.3±3.1 and 7.0±1.4 ng/g, respectively (n=4). A selected ion current chromatogram obtained from one of these analyses is shown in FIG. 9. Although:the levels,of $F_2$-IsoPs were slightly higher than the levels of $F_4$-NPs, these differences were not significant ($p>0.05$). However, levels of $F_4$-NPs esterified in the cortex of newborn pig brain (13.1±0.8 ng/g) greatly exceeded levels of $F_2$-IsoPs (2.9±0.4 ng/g) by a mean of 4.5-fold (n=3) ($p<0.0001$). Note that the pattern of $F_4$-NP peaks detected esterified in brain differs somewhat than that of compounds formed by oxidation of DHA in vitro. Slight differences were observed in the pattern of $F_2$-IsoPs formed from oxidation of arachidonic acid in vitro compared with that of compounds present esterified in tissue lipids. Although the reason for these differences has not been firmly established, a reasonable explanation for this is that there may be steric influences of phospholipids on the formation of different isomers from esterified substrate.

Figure 10:
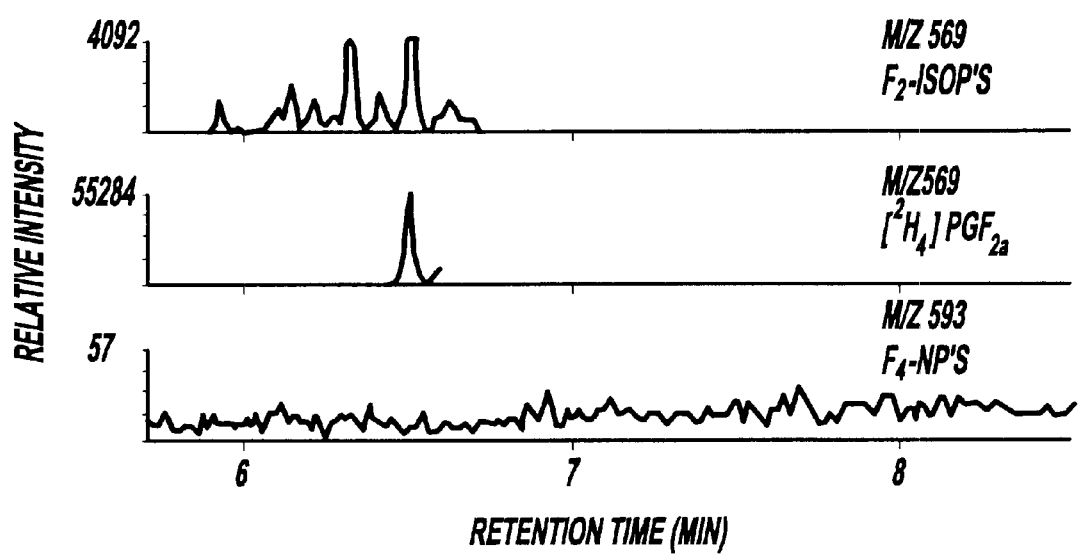
FIG. 10 is a selected ion current chromatogram obtained from the analysis for $F_2$-IsoPs and $F_4$-NPs esterified in lipids in 1 ml of plasma; the intense peaks present in the m/z 569 ion current chromatogram represent $F_2$-IsoPs; the peak in the m/z 573 ion current chromatogram representing the $[^2H_4]PGF_{2\alpha}$ internal standard; Absent are peaks in the m/z 593 ion current chromatogram representing $F_4$-NPs at a level above the lower limit of detection (~5 pg/ml)

As a measure of specificity of the assay to detect esterified $F_4$-NPs in tissues, $F_4$-NPs esterified were analyzed for in lipids in 1 ml of human plasma, which contains only very small amounts of DHA (FIG. 10) (Salem et al., 1986). Intense peaks were present in the m/z 569 ion current chromatogram representing $F_2$-IsoPs but absent were peaks of significant intensity in the m/z 593 ion current chromatogram that would indicate the presence of $F_4$-NPs at levels above the lower limits of detection (~5 pg/ml)

Figure 11:
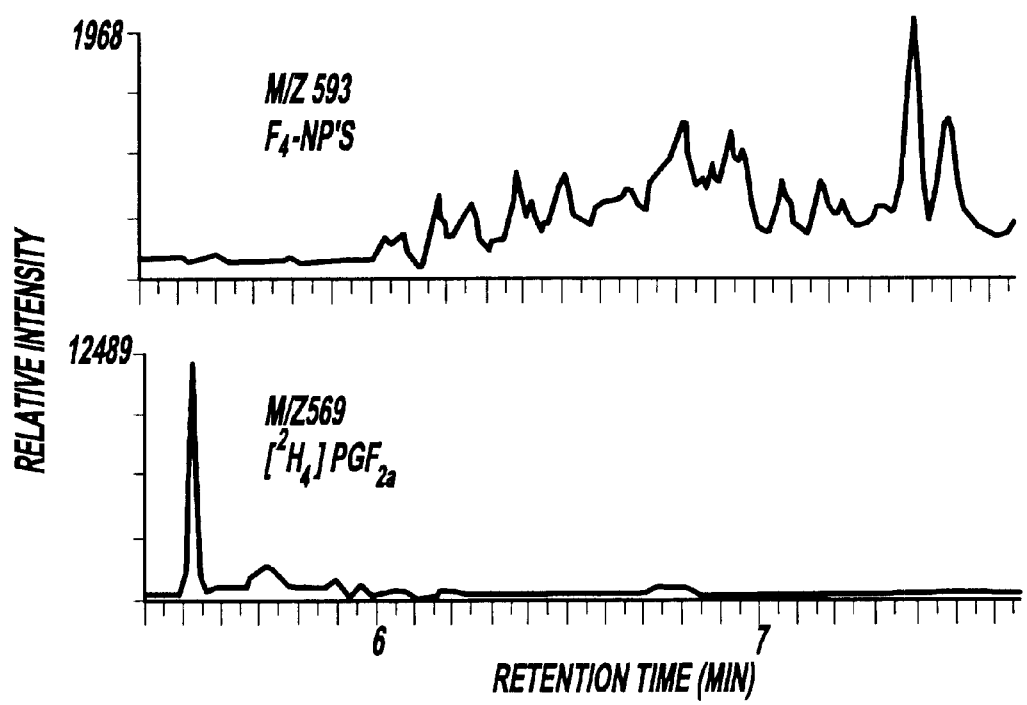
FIG. 11 shows selected ion current chromatogram. obtained from the analysis for $F_4$NPs in cerebrospinal fluid from a patent with Alzheimer's disease.

Although $F_4$-NPs can be readily detected esterified in the brain, the utility of such measurements to assess oxidative injury would primarily be restricted to animal models of neurological disorders or brain samples obtained postmortem from humans. It was therefore examined whether $F_4$-NPs could be detected in cereobrospinal fluid obtained from four patients with Alzheimer's disease and three age-matched control subjects. $F_4$-NPs were detected in 1–2 ml of cerebrospinal fluid from the control subjects at a level of 64±8 pg/ml. Of considerable interest was the finding that the concentrations measured in the patients with Alzheimer's disease were significantly higher (110±12 pg/ml) ($p<0.05$). A selected ion current chromatogram obtained from the analysis of $F_4$-NPs in cerebrospinal fluid from a patient with Alzheimer's disease is shown in FIG. 11. The pattern of $F_4$-NP peaks detected in free form in cerebrospinal fluid differs somewhat from the pattern peaks detected esterified in tissue phospholipids (FIG. 9). Similar differences have been observed for the pattern of $F_2$-IsoP peaks detected in free form in plasma and urine compared with the pattern of peaks detected esterified in tissue phospholipids as free compounds following base hydrolysis of a tissue lipid extract. Although the reason for these differences has not been established, this may be explained by differences in the efficacy of phospholipases to hydrolyze different isomers from phospholipids. Cerebrospinal fluid concentrations of $F_2$-IsbPs were similarly increased in patients with Alzheimer's disease but were lower than the levels of $F_4$-NPs in both control subjects and Alzheimer's patients (46±4 and 72±7 pg/ml, respectively).

Discussion

These studies have elucidated a new class of $F_2$-IsoP-like compounds formed in vivo by free radical-induced peroxidation of DRA. Free radical-induced peroxidation of AA results not only in the formation of F-ring IsoPs but also D-ring and E-ring IsoPs and thromboxane-like compounds (isothromboxanes) (Morrow et al., 1994; Morrow et al., 1996).

One of the motivations for determining whether IsoP-like compounds could be formed as peroxidation products of DHA involves the possibility that quantification of these compounds might provide a unique marker of oxidative injury in the brain that could be exploited to investigate the role of free radicals in the pathogenesis of neurological disease.

Although invasive, cerebrospinal fluid is frequently obtained for diagnostic purposes in patients with suspected neurological disorders. Thus, the availability of a marker of oxidative injury in the brain that could be measured in cerebrospinal fluid intra vitam would be an important advance. Thus, the finding that $F_4$-NPs can be detected in human cerebrospinal fluid clearly has potentially important clinical applications. It was shown that markers of lipid peroxidation are increased in cerebrospinal fluid of patients with Alzheimer's disease (Lovell et al, 1997; Montine et al, 1997). However, these assays have shortcomings related to measurement of reactive molecules, i.e., 4-hydroxynonenal, and require large volumes of fluid. However, $F_4$-NPs were detectable using negative ion chemical ionization mass spectrometry in 1–2 ml of cerebrospinal fluid from normal subjects, an amount that can usually be obtained safely from patients for diagnostic purposes. Although it was a limited study, the finding that $F_4$-NP concentrations in cerebrospinal fluid from patients with Alzheimer's disease were significantly higher than levels in age-matched control subjects highlights the potential of this approach to provide insights into the role of free radicals in the pathogenesis of neurological disorders. Another potentially important aspect of this finding is that serial measurements of $F_4$-NPs in cerebrospinal fluid might provide a biochemical assessment of disease. progression as well as a means to monitor efficacy of therapeutic intervention, e.g., with antioxidants, during life. No other method has proven to be reliable to obtain such information.

One question that arises is whether there is a distinct advantage of measuring either IsoPs or NPs to, assess oxidative injury in the brain. It is of interest that the relative amounts of $F_4$-NPs formed during oxidation of DHA in vitro exceeded the amounts of $F_2$IsoPs generated from an equivalent amount of AA by as much as 3.4-fold (FIG. 8). This is consistent with the fact that of the naturally occurring fatty acids, DHA is the most easily oxidizable (Dratz et al., 1986). This suggests that measurement of $F_4$-NPs in some situations may provide a more sensitive index of oxidative injury in the brain than measurement of $F_2$IsoPs. The ratio of levels of AA and DHA, and thus the capacity to form IsoPs and NPs, respectively, varies significantly between different regions of the brain (white matter, gray matter), different cell types (neurons, astrocytes, oligodendrocytes), and subcellular fractions (myelin, synaptosomes) (Salem et al., 1986; Skinner et al., 1993; Bourre et al., 1984). In this regard, it was found that levels of $F_4$-NPs and $F_2$IsoPs esterified in whole rat brain were similar, whereas levels of $F_4$-NPs were higher than levels of $F_2$IsoPs in the cortex of newborn pigs and in human cerebrospinal fluid. Therefore, there is distinct advantages associated with measuring either IsoPs or NPs to assess oxidant injury in the brain depending on the site of oxidant injury and the predominant cell types involved. Thus,.the best approach at this time, which will provide valuable insight into this question, would be to quantify both IsoPs and NPs in a variety of situations involving different types of oxidative insults to the brain both in experimental animals and in human neurological disorders. The practicality of this approach will be facilitated by the fact that the method of assay we developed allows simultaneous measurement of both $F_4$-NPs and $F_2$IsoPs in the same sample.

Figure 12:
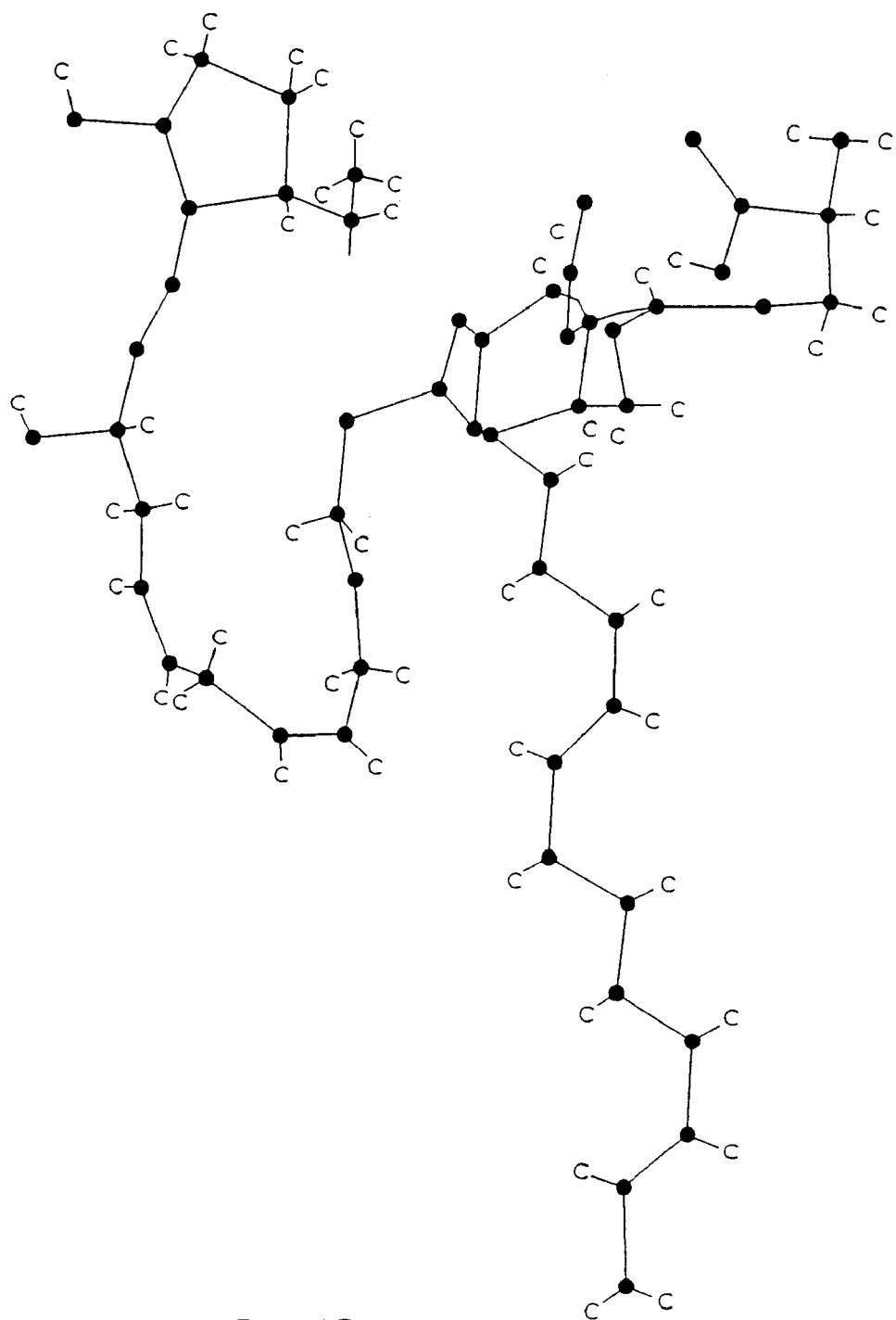
FIG. 12 shows a ball and wire molecular model of phosphatidylserine containing palmitate esterified in the sn-1 position and a 13-series NP(13-$F_{4t}$-NP) esterified in the sn-2 position; trailing downward on the right from the polar head group above is palmitic acid; trailing downward and the curving sharply upward on the left is the NP molecule in which the cyclopentane ring is seen at the top.
Figure 13:
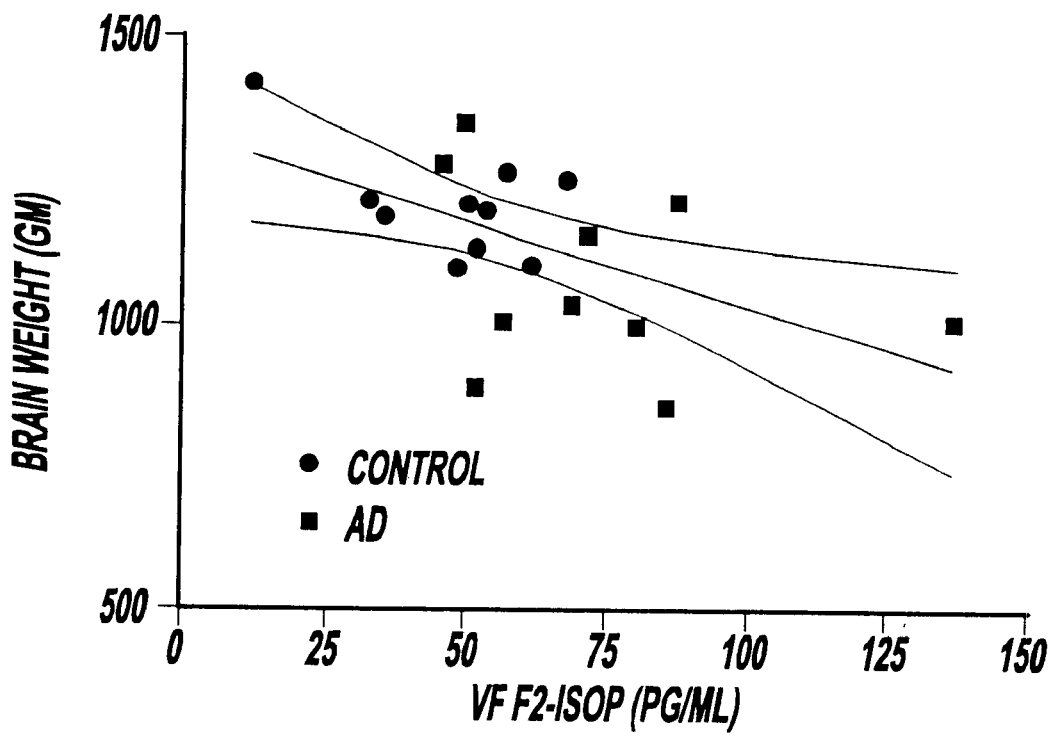
FIG. 13 shows a scatter plot of VF $F_2$-Isop concentration (pg/ml) versus brain weight (gm) for 22 control subjects and AD patients with best fit regression line and 95% confidence intervals ($r^2$=0.32, P<0.01)
Figure 14:
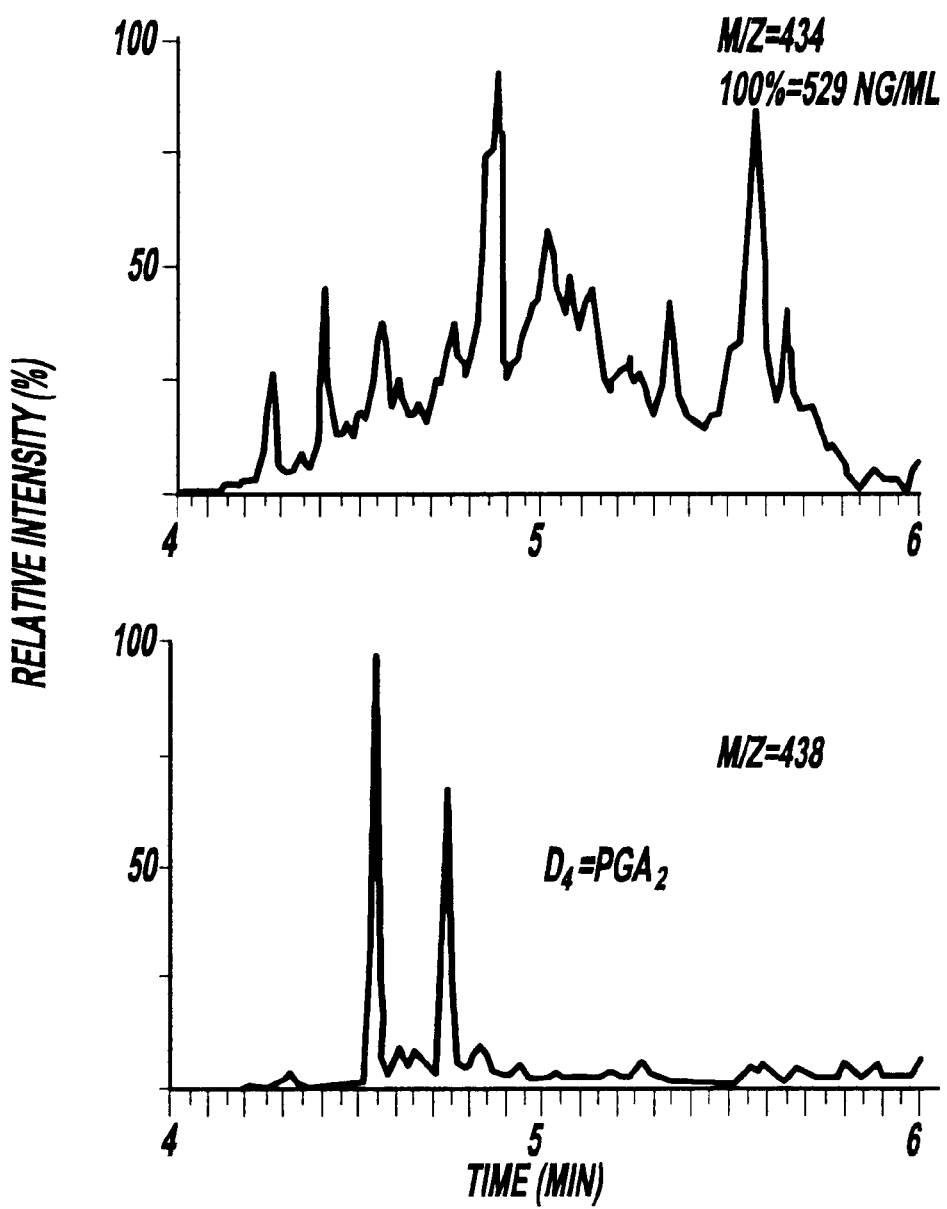
FIG. 14 shows selected ion current chromatograms from the analysis of the formation of $A_2/J_2$-IsoPs during oxidation of arachidonic acid in vitro. The peaks in the m/z 438 ion current chromatogram represent the syn- and anti-O-methyloxime isomers of the $[^2H_4]PGA_2$ internal standard; in the m/z 434 chromatogram being a series of peaks consistent with the presence of $A_2/J_2$-IsoPs; the summed total amount of the putative $A_2/J_2$-IsoPs formed being 529 ng/mg of arachidonic acid.
Figure 15:
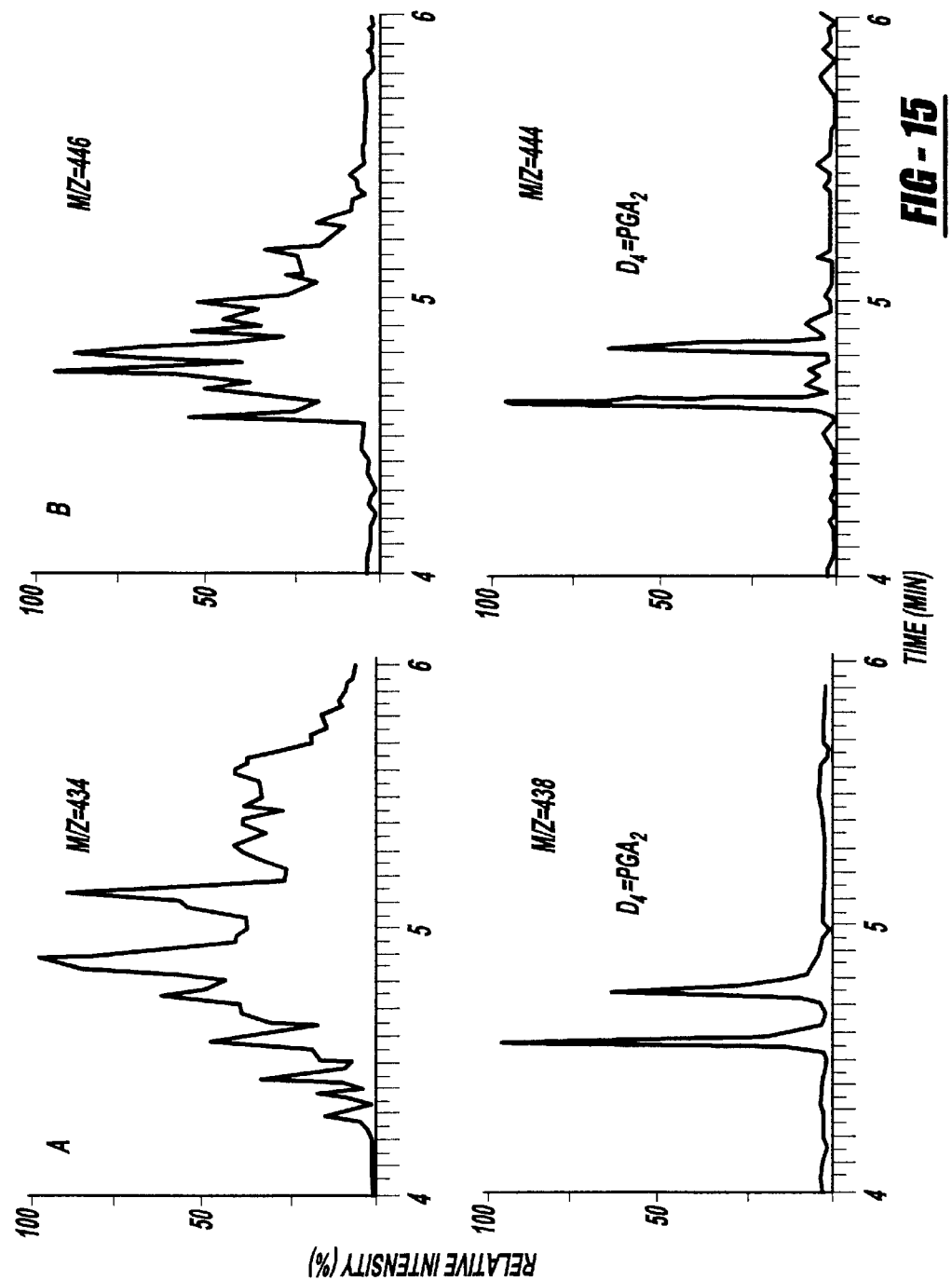
FIGS. 15A and B are an analysis of the putative $A_2/J_2$-IsoPs formed during oxidation of arachidonic acid in vitro prior to and after catalytic hydrogenation. A, analysis of compounds prior to hydrogenation; the peaks in the m/z 434 ion current chromatogram representing putative $A_2/J_2$-IsoPs, and the peaks in the m/z 438 chromatogram representing the $[2H_4]PGA_2$ internal standard; no compounds being detected six Da above m/z 434 at m/z 440 prior to hydrogenation; B, analysis of compounds following hydrogenation; both the internal standard and the m/z 434 peaks in A having shifted upwards six Da following hydrogenation, indicating the presence of three double. bonds;.
Figure 16:
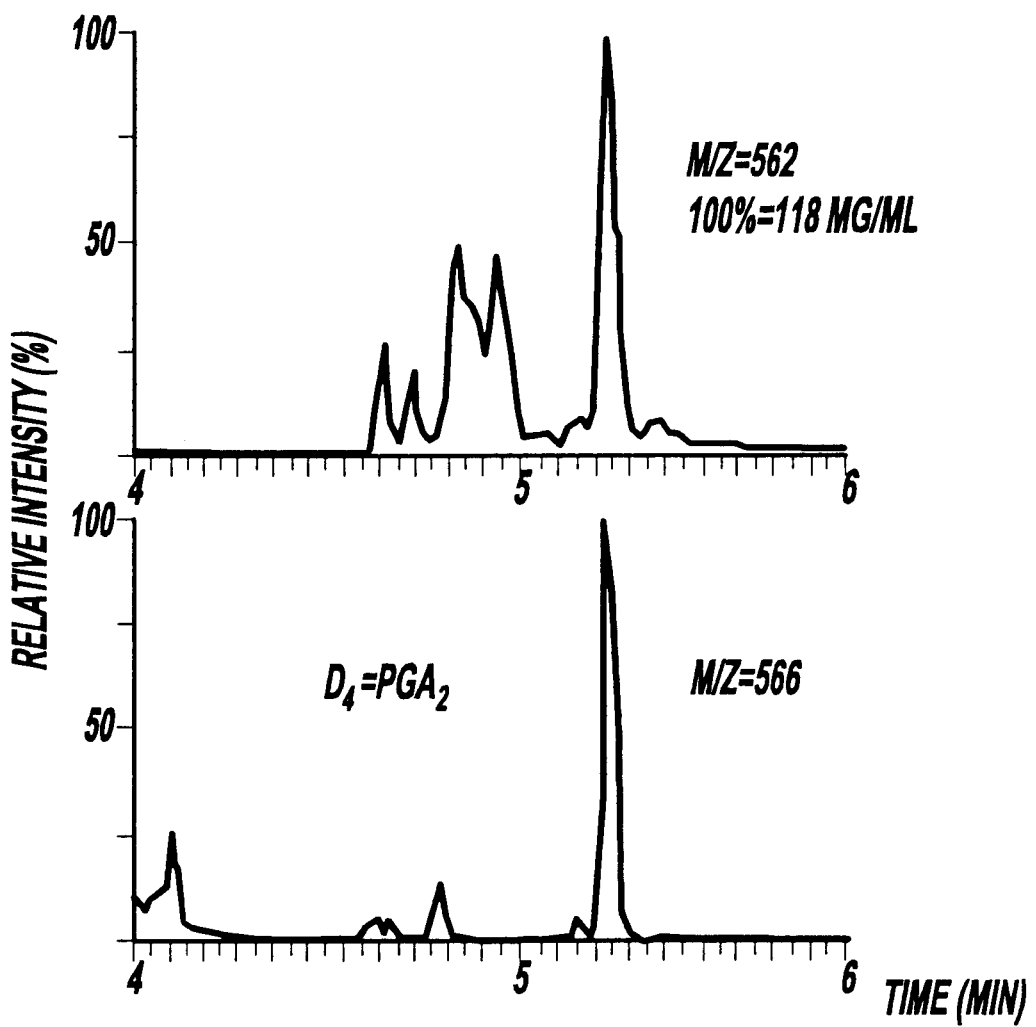
FIG. 16 is an analysis of $A_2/J_2$-IsoPs generated during oxidation of arachidonic acid in vitro as a PFB ester, piperidyl-enol-TMS ether derivative; the peaks in the m/z 566 chromatogram representing the $[^2H_4]PGA_2$ internal standard; in the m/z 562 chromatogram being a series of peaks consistent with the formation of a piperidyl-enol-TMS ether derivative of CP-IsoPs.
Figure 17:
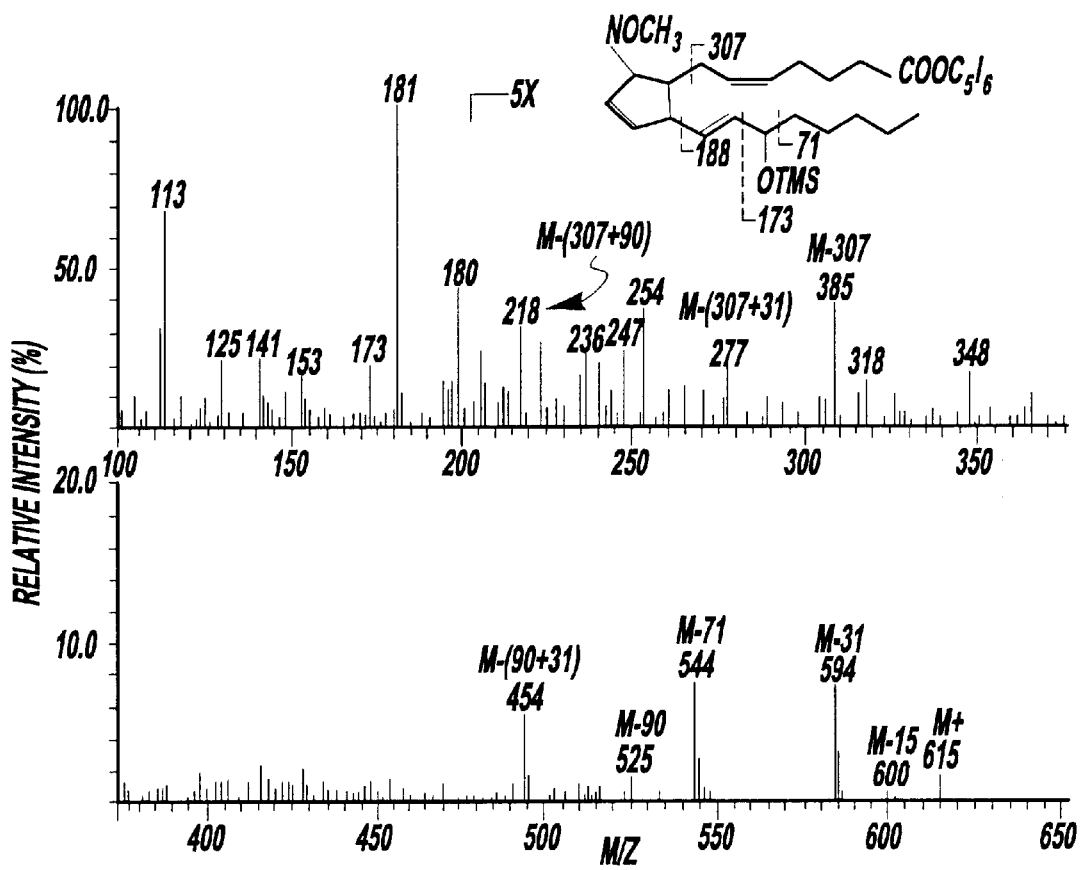
FIG. 17 shows a representative electron ionization mass spectrum obtained from the analysis of $A_2/J_2$-ISoPs generated from oxidation of arachidonic acid in vitro as a PFB ester, O-methyloxime, TMS ether derivative.
Figure 18:
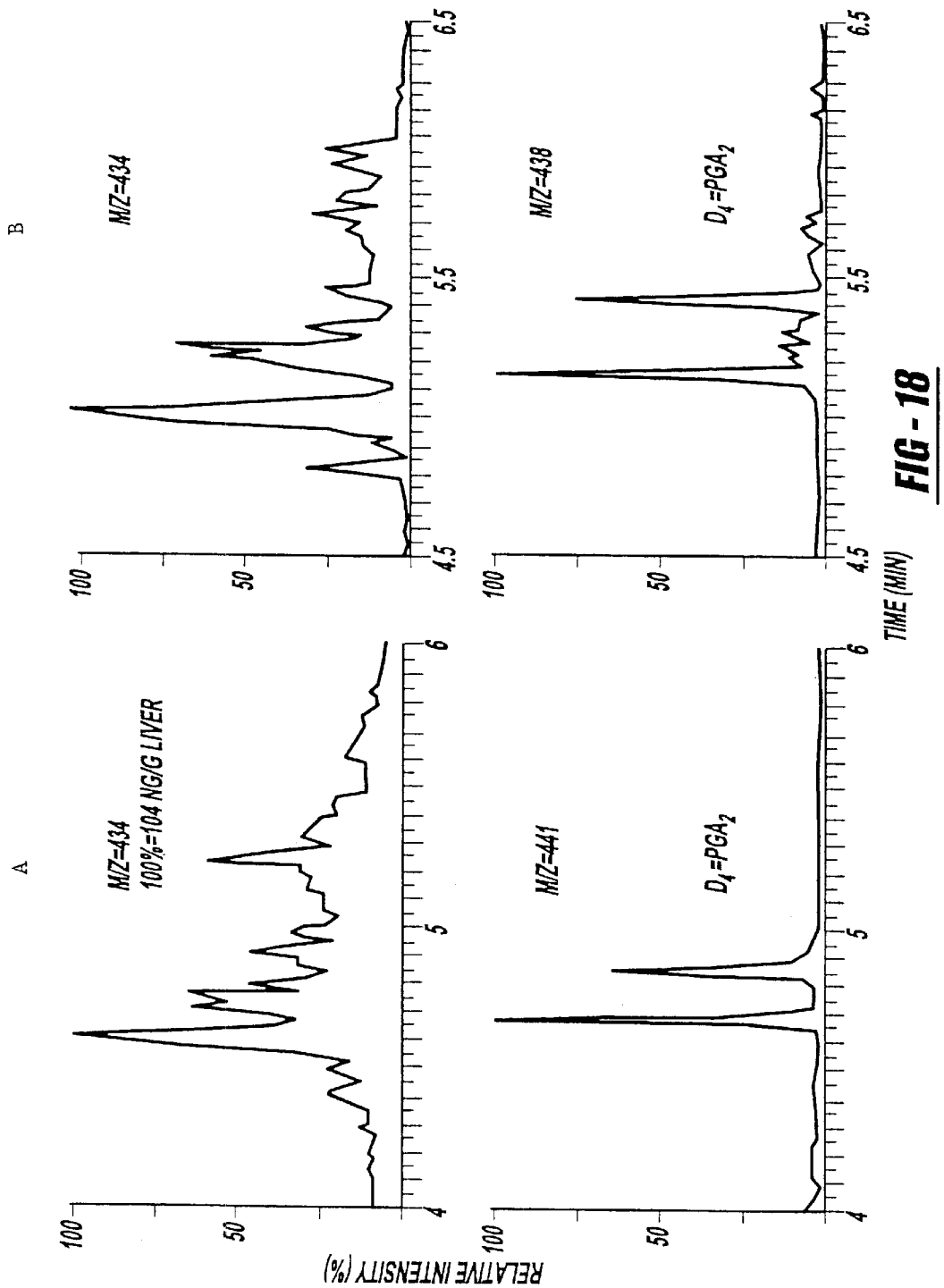
FIG. 18A is an analysis of $A_2/J_2$-IsoPs formed in vivo esterified in lipids in the liver of a rat treated with $CCl_4$; the peaks in the m/z 441 ion current chromatogram representing the $[^2H_4]PGA_2$ internal standard; in the m/z 434 ion current chromatogram being a series of peaks consistent with the presence of $A_2/J_2$-IsoPs; B. analysis of $A_2/J_2$-IsoPs following oxidation of arachidonoyl-phosphatidylcholine in vitro; in the m/z 434 chromatogram is a series of peaks consistent with the presence of $A_2/J_2$-IsoPs in a pattern that is very similar to the pattern of peaks detected in rat liver.
Figure 19:
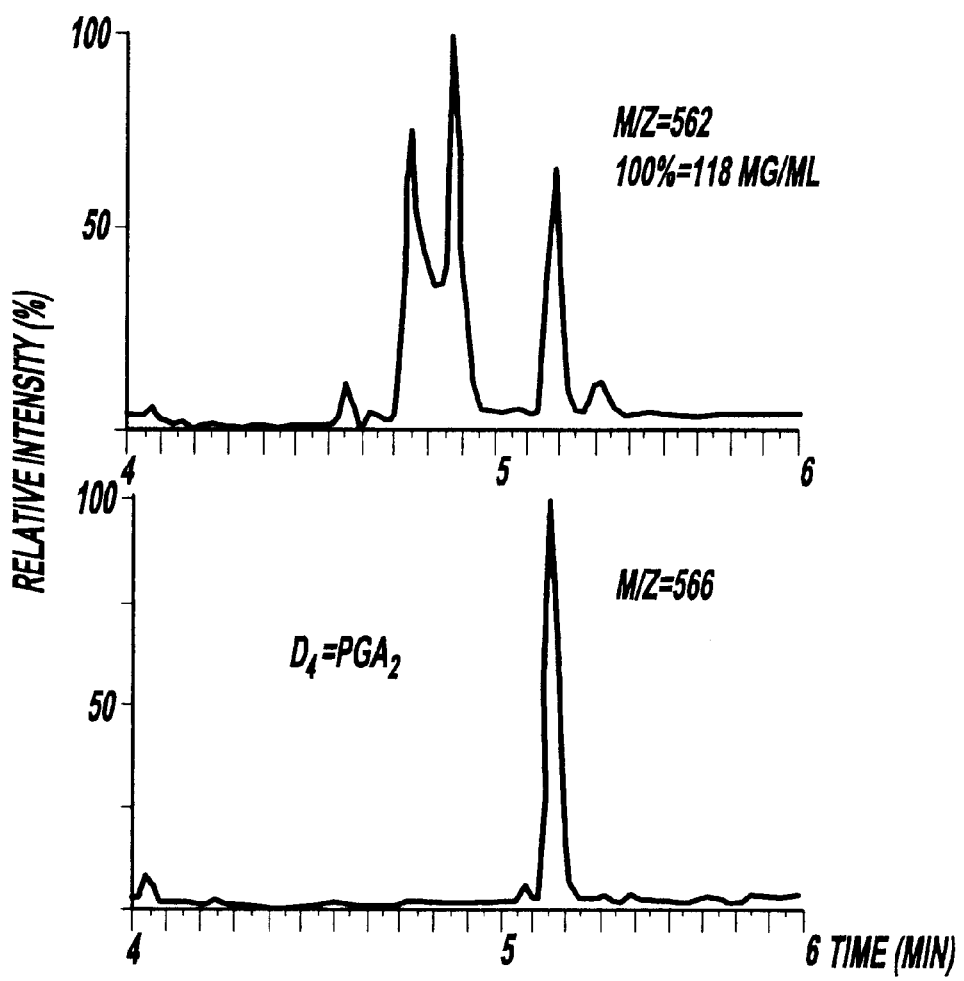
FIG. 19 shows an analysis of CP-IsoPs esterified in the liver of a rat treated with $CCl_4$ as a PFB ester, piperidylenol-TMS ether derivative, the peaks in the m/z 562 ion current chromatogram representing CP-IsoPs, and the m/z 566 peaks represent the $[^2H_4]PGA_2$ internal standard.
Figure 20:
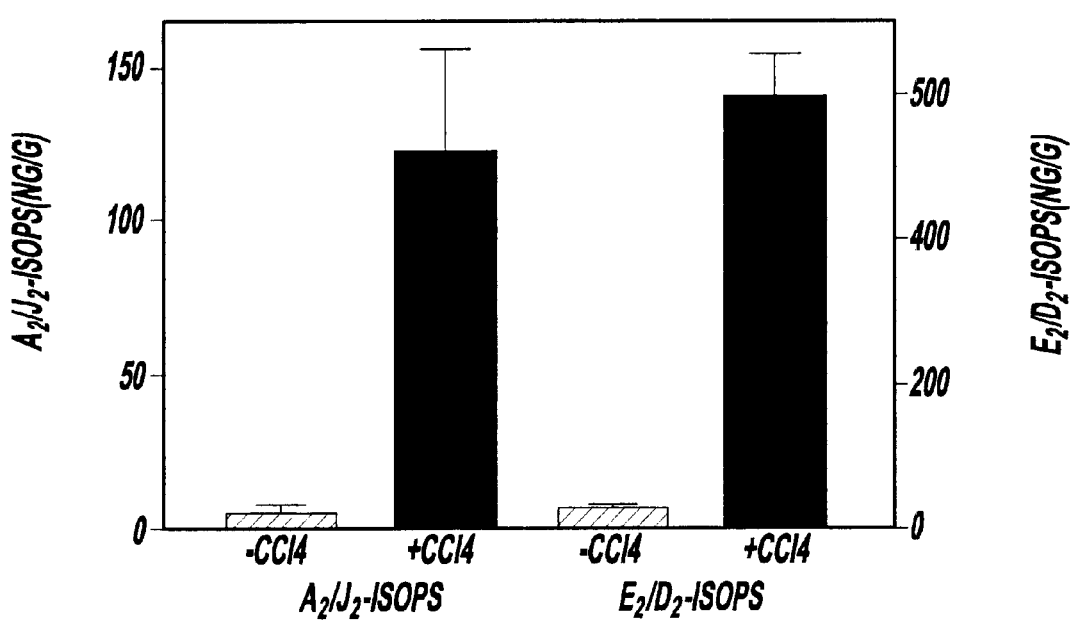
FIG. 20 shows an analysis of CP-IsoPs and $D_2/E_2$-IsoPs esterified in livers from normal rats and following administration of $CCl_4$, to induce an oxidant injury to the liver.
Figure 21:
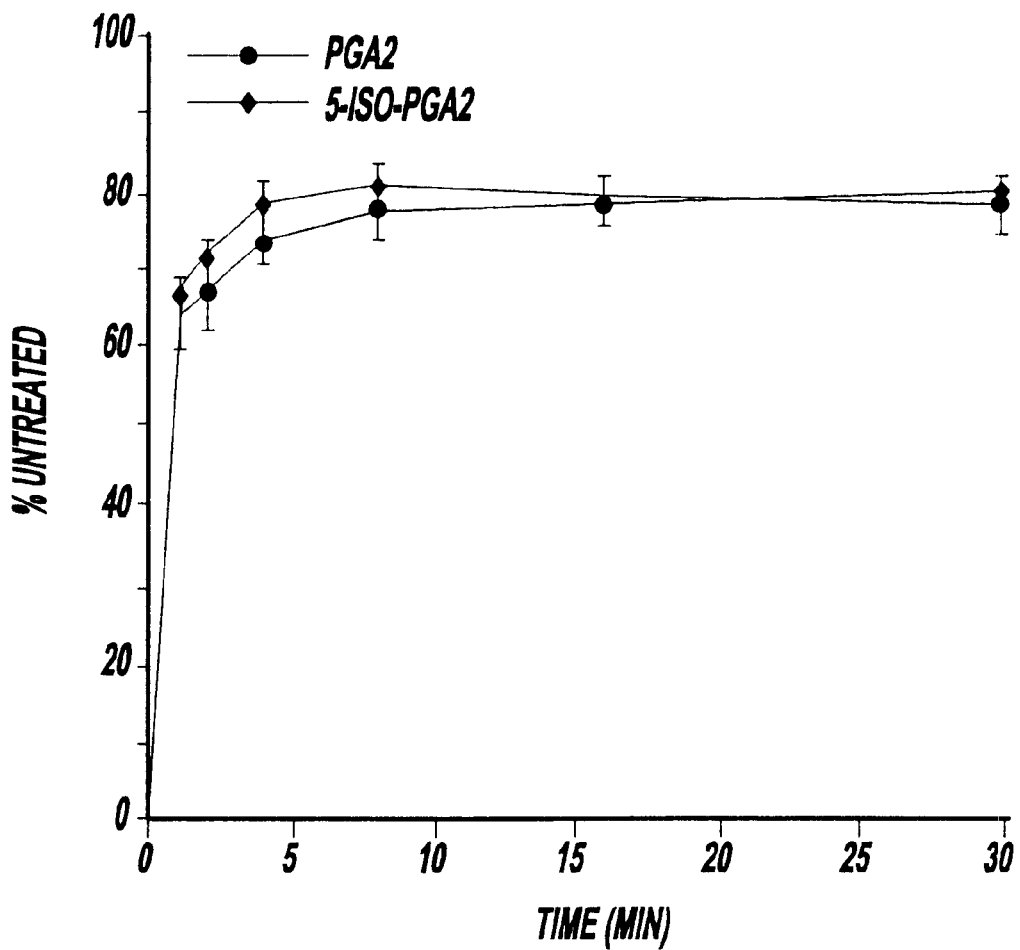
FIG. 21 shows a time course of GSH-catalyzed conjugation of 15-$A_{2t}$-IsoP and $PGA_2$ with GSH, formation of polar-GSH conjugates being monitored over time and being expressed as the percent of total radioactivity that did not extract into methylene choloride.
Figure 22:
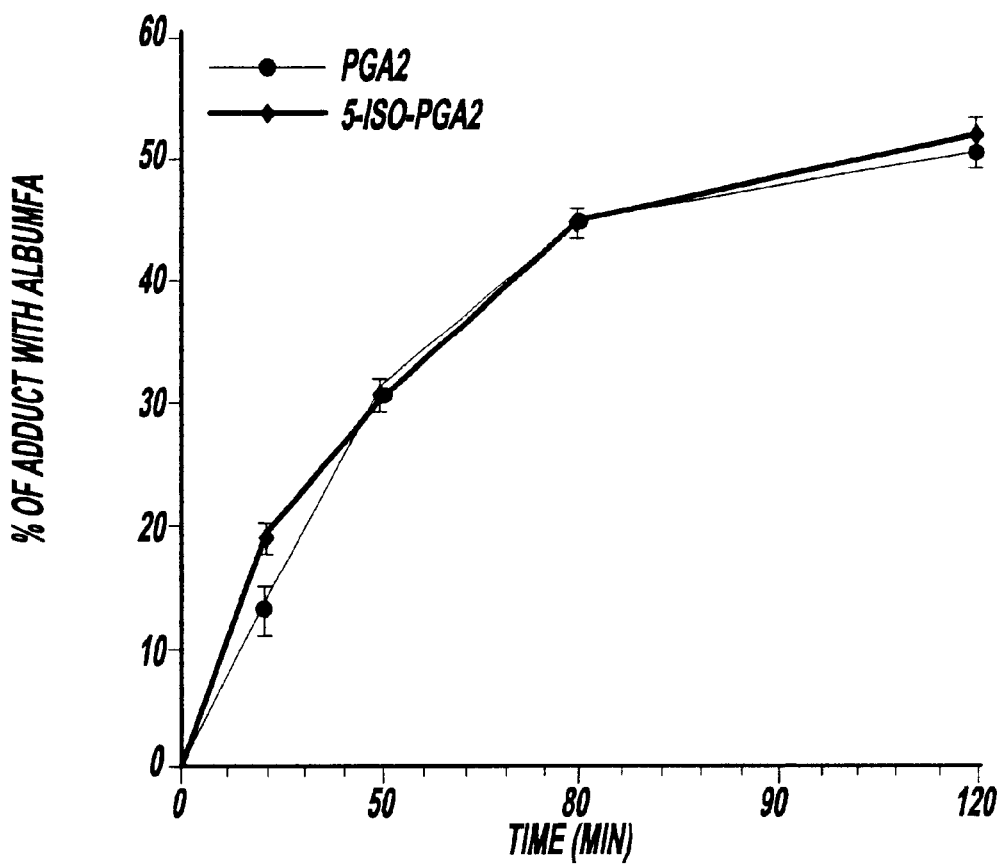
FIG. 22 shows a time course of covalent adduction of 15-$A_{2t}$-IsoP and $PGA_2$ with albumin; formation of the adducts being monitored over time and is expressed as the percent of total radioactivity present in the protein pellet following precipitation with cold ethanol.

There are additional ramifications that are potentially relevant to neuropathobiology that emerge from this discovery. Two of the IsoPs, previously referred to as 8-iso-PGF$_{2\alpha}$ and 8-iso-PGE$_2$, now termed 15-$F_{2t}$-IsoP and 15-E2t-IsoP according to the approved nomenclature for IsoPs (Taber et al., 1997), have been found to possess potent biological activity ranging from effects on vascular and bronchial smooth muscle, endothelin release, platelet function, to cellular proliferation.(Roberts et al., 1997; Morrow et al., 1997). Of interest has been the evidence obtained which suggests that these IsoPs exert their vascular effects by interacting with a unique receptor (Roberts et al., 1997; Morrow et al., 1997). Thus, NPs also are found to possess important biological actions that may be relevant to the pathophysiology of oxidant injury to the brain. As mentioned, this is greatly supported by the finding that C22-PGF$_{4\alpha}$ is bioactive (Salem et al., 1986). This compound is one of the $F_4$-NPs that would be formed, although, analogous to IsoPs, compounds in which the side chains are oriented cis likely predominate over compounds in which the side chains are oriented trans in relation to the cyclopentane ring (Morrow et al., 1990). However, in the case of the IsoPs, inversion of the stereochemistry of the upper side chain of PGF$_{2\alpha}$ and PGE$_2$ affords different and/or more potent biological actions (Roberts et al., 1997; Morrow et al., 1997);

In addition, phospholipids containing esterified NPs are very unnatural and unusual molecules. Shown in FIG. 12 is a molecular model of phosphatidylserine with palmitate esterified at the sn-1 position and a 13-series NP (13-$F_{4t}$-NP) esterified at the sn-2 position. Mass spectral evidence for the formation of 13-series $F_4$-NPs during oxidation of DHA was presented in FIG. 6. Trailing downward on the right from the polar head group above is palmitic acid. Trailing downward and then curving sharply upward on the left is the NP molecule in which the cyclopentane ring is seen at the top. Unmistakably, this is a remarkably distorted molecule. Thus, enhanced formation of these unusual phospholipids in neuronal membranes in settings of oxidant injury to the brain might lead to profound alterations in the biophysical properties of the membrane, e.g. degree of fluidity, which in turn might greatly impair normal, neuronal function.

EXAMPLE 2

Methods and Materials

CSF from 24 different subjects was collected following appropriate informed consent. Twenty-two subjects had autopsies performed in 1996 or 1997. All AD patients had been diagnosed with probable AD during life. Control subjects were age-matched individuals without clinical evidence of dementia or other neurological disease; each of these individuals had annual neuropsychological testing with all test scores in the normal range. Ventricular CSF (VF) was collected from each subject as part of a rapid autopsy protocol. Mean post mortem intervals were 2.9±0.3 hour in control subjects and 2.7±0.2 hour in AD patients; all samples were collected within 4.5 hours of death. APOE genotype was determined post mortem in all cases (Saunders et al., 1993).

Immediately following aspiration, VF was sedimented at 1000×g for 10 minutes and 1 to 2 ml were frozen at −80° C. There was no visual contamination of aspirates with blood, nor was apolipoprotein B detected in immunoblots of VF (Montine et al., 1997). Brains were evaluated using standard criteria (Khachaturian, 1985; Mirra et al., 1991). Patients with brainstem or cortical Lewy body formation, or significant. cerebrovascular disease were excluded. Control subjects demonstrated only age-associated alterations. Braak staging was performed on all cases (Braak, 1991).

CSF aspirated intra vitam from the lumbar cistern (LF) was analyzed in two additional patients. Both of these patients were being evaluated for neurological disease and LF was obtained for diagnostic purposes. Both samples were free of contamination by blood and had standard clinical chemistry values within normal ranges. Ultimate diagnoses for these two patients were optic neuritis and malignant lymphoma. LF was handled and stored as described for VF.

Free $F_2$IsoP in 1 to 2 ml of CSF were quantified using stable isotope dilution methods employing gas chromatography/negative ion chemical ionization mass spectrometry (GC/NICIMS) as described (Morrow et al., 1990; Morrow et al., 1997). In seven patients, $F_2$-IsoP-like compounds were quantified that are derived from docosahexaenoic acid, the $F_4$-neuroprostanes ($F_4$-NP); these were quantified by a modification of the above GC/NICIMS method as described (Roberts et al., 1997).

Hypothesis testing for continuous data was performed with unpaired t-tests. Discontinuous data were compared with the chi-squared test. Single dimension linear regression analysis and Spearman's ranked correlation were performed using Prism 2.0 software.

Results

All 22 VF samples analyzed in this study were from subjects who participated in a rapid autopsy program. Clinical, pathological, and $F_2$-IsoP data for these 22 cases are presented in the-Table 2. Age and gender ratios were characteristic for patients with late-onset AD and were matched to control subjects. Duration of disease was typical for the group of AD patients. Brain weight was significantly lower while Braak stage was significantly higher in AD patients compared to control subjects. APOE4 frequency in control subjects was similar to the value reported for the general population (Mahley, 1988).

Average VF $F_2$-IsoP levels in AD patients were significantly increased compared to control subjects (Table 2). The ranges of VF $F_2$-IsoP values were 12 to 68 pg/ml in control subjects and 46 to 137 pg/ml in AD patients. Single dimension linear regression analysis demonstrated a significant correlation between $F_2$-IsoP levels and brain weight (−0.3 pg/ml per gm, $r^2$=0.32, P<0.01, Figure), but not with subjects' age ($r^2$=0.06), body weight (0.04), or post mortem interval ($r^2$=0.01). $F_2$-IsoP levels tended to increase with increasing duration of dementia; however, this relationship was not statistically significantly in these 11 AD patients. Ranked Correlations showed that increasing $F_2$-IsoP levels were significantly correlated with increasing Braak stage (P<0.001), but not the number of APOE4 alleles, for all 22 subjects. When analysis was restricted to AD patients only, neither Braak stage nor the number of APOE4 alleles was significantly correlated with $F_2$-IsoP levels.

Recently, a series of $F_2$-IsoP-like compounds derived from peroxidation docosahexaenoic acid were described (Roberts et al., 1997); because docosahexaenoic acid is found primarily in the CNS, these compounds are termed $F_4$-neuroprostanes ($F_4$-NP). There was sufficient VF available for analysis of $F_4$-NP levels in four of the AD patients and three control subjects. Indeed, average VF $F_4$-NP levels were 110±12 pg/ml in these AD patients and 64±8 pg/ml in control subjects (P<0.05). VF $F_2$-IsoP and $F_4$-NP levels showed near perfect linear correlation in these seven subjects ($r^2$=0.97, P<0.001).

In order to establish the feasibility of determining CSF $F_2$-IsoP levels during life, CSF aspirates were analyzed from the lumbar cistern (LF) in two additional patients with suspected neurological disease but normal CSF. LF free $F_2$-IsoP levels in-these two patients were 30 and 32 pg/ml, approximating the V levels in control subjects and demonstrating the potential of measuring $F_2$-IsoP levels during life.

Discussion

AD is associated with increased lipid peroxidation in diseased regions of brain that have been studied post mortem. While this approach has the advantage of coupling biochemical data with pathological verification of AD, two critical disadvantages have been that the assays used cannot be easily performed intra vitam and. many are not entirely specific for lipid peroxidation. In the present study, free $F_2$-IsoP concentrations were measured, specific products of free radical-catalyzed peroxidation of arachidonic acid, in CSF from clinically and pathologically defined subjects. The results showed that average VF $F_2$-IsoP levels in AD patients were significantly greater than in carefully documented control subjects. Moreover, VF $F_2$-IsoP levels were inversely correlated with brain weight. Also, in a limited manner, the feasibility of measuring $F_2$-IsoPs intra vitam was demonstrated in CSF aspirates from lumbar cistern. There was no correlation between VF $F_2$-ISoP levels and the number of APOE4 alleles in the study; however, the number of patients was small and this lack of association with APOE genotype will need to be addressed definitively in a larger series of patients.

In the present study, $F_2$-IsoP levels in VF from control subjects were similar to average plasma levels in healthy human volunteers (Morrow et al., 1997), raising the possibility that free $F_2$-IsoP equilibrates between plasma and intrathecal compartments and suggesting that VF $F_2$-IsoP in control subjects is derived, at least in part, from plasma. However, several points argue that elevated VF $F_2$-IsoP levels in AD patients are derived from brain. First, numerous studies have consistently associated AD with regionally increased oxidative damage to brain (Markesbery, 1997), but have not consistently observed evidence of increased systemic oxidative stress (Markesbery, 1997; Ahlskog et al., 1995). Also, in the present study coincident elevations in VF $F_4$-NP and $F_2$-IsoP concentrations were demonstrated, the former being derived from docosahexaenoic acid that is extensively enriched in the CNS (Kuksis, 1978).

CSF $F_2$-IsoP concentration can serve as a biomarker of CNS lipid peroxidation in patients with AD. There is no other quantifiable biomarker of AD that is significantly correlated with reduced brain weight, a manifestation of cerebral atrophy, and that can be measured during life. Quantification of CSF $F_2$-IsoP concentration has utility as an intra vitam index of disease progression or response to therapeutic intervention.

EXAMPLE 3

Frontal-lobes of brain from aged 9 month old female apoE −1− mice backbred eight generations to the C57B6/J strain and identically aged C57B6/J wild type mice were examined and determined total lipid content as well as $F_2$-isoP and $F_4$-neuroP levels. There were no differences in the tissue concentrations of phospholipid, cholesterol, triglyceride, or eight different fatty acids including AA and DHA, the substrates for isoP's and neuroP's, respectively In contrast, both $F_2$-isoP and $F_4$-neuroP tissue concentrations were significantly elevated in the same region of brain of apoE −1− mice. The concentration of DHA was three times greater than AA in apoE +/+ and apoE −1− mice. In contrast, the ratio of $F_4$-neuroP to $F_2$-isoP is 82 in apoE +/+ mice and 190 in apoE −1− mice, consistent with our in vitro observation that DHA is more vulnerable to oxidation than AA. The D+E ring forms for isoP's and neuroP's have not been measured in these mice.

|  | AA (ug/mg) | DHA (ug/mg) | $F_2$-isoP (pg/mg) | $F_4$-neuroP (pg/mg) |
|---|---|---|---|---|
| apoE +/+ | 2.0 ± 0.3 | 5.9 ± 0.9 | 1.7 ± 0.3 | 140.4 ± 48.3 |
| apoE −/− | 1.9 ± 0.2 | 5.7 ± 0.8 | 2.4 ± 0.2* | 455.8 ± 122.6* |

Nine month old mice, either apoE −/− or wild type controls, were sacrificed and one frontal lobe used to determine AA and DHA levels while the other frontal lobe was used to quantify $F_2$-isoP and $F_4$-neurop levels. All values are means±SEM with n=4 different animals. *P≦0.01 for t-test comparing values from apoE −/− with apoE +/+ animals.

Human Subjects. Complete absence of apoE as in apoE −/−mice obviously is distinct from inheriting different apoE isoforms. Neuronal culture experiments have indicated that apoE isoforms have varying anti-oxidant activities with apoE2>apoE3>apoE4. Studies in human subjects have observed trends, although not statistically significant, toward increased levels of lipid peroxidation with inheritance of APOE4; however interpretation has been limited by the indirect and nonspecific indices used and by small sample sizes.

Ongoing experiments in the laboratory designed to develop CSF $F_2$-isoP's and $F_4$-neuroP's as biomarkers of brain lipid peroxidation in living patients have established the feasibility of the tissue-based studies proposed here. For these experiments, CSF was obtained post mortem from the lateral ventricles as part of a rapid autopsy protocol and was shown to be free of red blood cells or detectable apoB. Elevated $F_2$-IsoP levels were demonstrated in CSF of AD patients compared to carefully characterized age-matched control subjects. More importantly, CSF $F_2$-isoP levels are inversely correlated with brain weight (an index of brain atrophy, FIG. 8) and positively correlated with Braak stage (a histopathological index of AD severity) providing the first in vivo evidence that brain lipid peroxidation may be part of the progression of AD. In a limited number of patients, significantly increased neuroP's were demonstrated in AD patients compared to controls.

TABLE

|  | Age (yr) | Female to Male | Brain weight (g) | Braak Stage | Alleles as APOE4 | $F_1$-isoP (pg/ml) |
|---|---|---|---|---|---|---|
| Control (n = 11) | 82.2 ± 1.8 | 8:3 | 1233 ± 32 | 1.7 ± 0.4 | 12% | 46 ± 4 |
| AD (n = 11) | 78.4 ± 1.6 | 7:4 | 1090 ± 51* | 5.8 ± 0.1# | 50% | 72 ± 7+ |

Values are means ± SEM, percentage of APOE4 with respect to total number of APOE alleles, or the number of male and female subjects. Unpaired t-test yielded #P = 0.05, +P = 0.01, or #P < 0.001 for control subjects vs AD patients as indicated. Ages of AD patients and control subjects were not significantly different.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims, the invention may be practiced otherwise than as specifically described.

TABLE I

Levels of $F_2$-IsoPs and $F_4$-NPs measured esterified to lipids in whole normal rat brain (n = 4) and in brain cortex from newborn pig (n = 3)
$F_2$-IsoPs and $F_4$-NPs were measured as free compounds following base hydrolysis of a Folch lipid extract of brain tissue as described under "Experimental Procedures.∞ The data are expressed as nanograms of $F_2$-IsoPs and $F_4$-NPs measured per g of wet weight of tissue.

|  | $F_2$-IsoPs | $F_4$-NPs | p value ($F_2$IsoP vs $F_4$-NP) |
|---|---|---|---|
|  | ng/g | | |
| Whole brain from normal rat | 10.3 ± 3.1 | 7.0 ± 1.4 | >0.05 |
| Brain cortex from newborn pig | 2.9 ± 0.4 | 13.1 ± 0.8 | <0.0001 |

TABLE 2

Clinical, Pathological, and $F_2$-isoP Data for Subjects with Post Mortem Examination

|  | Age (yr) | Female to Male | Duration of disease (yr) | Brain weight (g) | Braak Stage | % alleles as APOE4 | $F_2$-IsoP (pg/ml) |
|---|---|---|---|---|---|---|---|
| Control (n = 11) | 82.2 ± 1.8 | 8:3 | 0.0 | 1233 ± 32 | 1.7 ± 0.4 | 12% | 46 ± 4 |
| AD (n = 11) | 78.4 ± 1.6 | 7:4 | 7.2 ± 1.2 | 1090 ± 51* | 5.8 ± 0.1# | 50%^ | 72 ± Z+ |

REFERENCES

Ahlskog J, Utti R, Low P, Tyce G, Nickander K, Petersen R, and Kokmen E. No evidence for systemic oxidant stress in Parkinson's or Alzheimer's disease. Movement Disorders 1995; 10:566–73.

Atsmon, J., Sweetman, B. J., Baertschi, S. W., Harris, T. M., and Roberts, L. J. (1990) *Biochemistry* 29, 3760–3765.

Attallah, A., Payakkapan, W., Lee, J., Carr, A., and Brazelton, E. (1974) *Prostaglandins* 5, 69–71.

Bourre, J. M., Pascal, G., Durand, G., Masson, M., Dumont, O., and Piciotti, J. (1984) *U. Neurochem.* 43, 342–348.

Boyland, E., and Chasseaud, L. F. (1968) *Biochem, J.* 109, 651–661.

Braak H and Braak E. Neuropathological standing of Alzheimer-related changes. Acta Neuropathol 1991; 82–239–59.

Bui, T., and Straus, D. S. (1998) *Biochem. Biophys. Acta.* 1397, 31–42.

Conner, W. E., Neuringer, M., and Reisbick, S. (1992) *Nutri Rev.* 50, 21–29.

Dratz, E. A., and Deese, A. J. (1986) *Health Effects of Polyunsaturated Fatty Acids in Seafoods* (Simopoulos, A. P., Kifer, R. R., and Martin, R. E., eds) pp. 319–351, Academic Press, Orlando, Fla.

Forman, B. M., Tontonoz, P., Chen, J., Brun, R. P., Spiegelman, B. M., and Evans, R. M. (1995) *Cell* 83, 803–812.

Fukushima, J. (1992) *Prostaglandins Leukotrienes Essent. Fatty Acids* 47, 1–12.

Fukushima, M. (1990) *Eicosanoids* 3, 189–199.

Hirata, Y., Hayashi, H., Ito, S., Kikawa, Y., Ishibashi, M., Sudo, M., Miyazaki, H., Fukushima, M., Narumiya, S., and Hayaishi, O (1988) *J. Biol. Chem.* 263, 16619–16625.

Honn, K. V., and Marnett, L. J. (1985) *Biochem. Biophys. Res. Commun.* 129, 34–40.

Jonsson, H. T., Middleditch, B. S., Schexnayder, M. A., and Desiderio, D. M. (1976) *J. Lipid. Res.* 17, 1–6.

Khachaturian, Z. S. Diagnosis of Alzheimer's disease. (1985) *Arch. Neurol.* 42, 1097–1105.

Kim, I. -K., Lee, J. -H., Sohn, H. -W., Kim, H. -S., and Kim, S. -H. (1993) *FEBS Lett.* 321, 209–214.

Kliewer, S. A., Lenhard, J. M., Willson, T. M., Patel, I., Morris, D. C., and Lehmann, J. M. (1995) *Cell* 83, 813–819.

Knight, J. A. (1997) *Ann. Clin. Lab. Sci.* 27, 11–25.

Kuksis A. Fatty acid composition of glycerolipids of animal tissues. *Handbook of Lipid Research.* Edited by A. Kuksis. New York, Plenum Press, 1978, p. 381–442.

Longmire, A. W., Swift, L. L., Roberts, L. J., II, Awad, J. A., Burk, R. F., and Morrow, J. D. (1994) *Biochem. Pharmacol.* 47, 1173–1177.

Lovell, M., Ehmann, W., Mattson, M., and-Markesbery, W. Elevated.4-hydroxynonenal in ventricular fluid in Alzheimer's disease. (1997) *Neurobiol. Aging* 18, 457–461.

Mahley R W. Apolipoprotein E: cholesterol transport protein with expanding role in cell biology. Science 1988; 240:622–630.

Markesbery, W. R. (1997) *Free Radic. Biol. Med.* 23, 134–147.

Markesbery, W. R. Oxidative stress hypothesis in Alzheimer's disease. Free Radic Biol Med 1997; 23:134–147.

Melegos, D. M., Diamandis, E. P., Oda, H., Urade, Y., and Hayaishi, O. (1996) *Clin. Chem.* 42, 1984–1991.

Middledtich, B. S., (1975) *Prostaglandins* 9, 409–411.

Mirra, S. S., Heyman, A., McKeel, D., Sumi, S. M., Crain, B. J., Brownlee, L. M., Vogel, F. S., Hughes, J. P., van Belle, G., and Berg, L. The Consortium to Establish a Registry for Alzheimer's Disease (CERAD). Part II. Standardization of the neuropathologic assessment of Alzheimer's disease. (1991) *Neurology* 41, 479–486.

Montine, T. J., Montine, K. S., and Swift, L. L. Central nervous system lipoproteins in Alzheimer's disease (1997) *Am. J. Pathol.* 151, 1571–1575.

Moore, S. A., Yoder, E., Murphy, S., Dutton, G. R., and Spector, A. A. (1991) *J. Neurochem.* 56, 518–524.

Morrow, J. D., and Roberts, L. J., II (1994) *Methods Enzymol.* 233, 163–174.

Morrow, J. D., and Roberts, L. J., II The isprostanes: unique bioactive products of lipic peroxidation. (1997) *Prog. Lipid Res.* 36, 1–21.

Morrow, J. D., Awad, J. A., Boss, H. J., Blair, I. A., and Roberts, L. J., II. (1992) *Proc. Natl. Acad. Sci. U.S.A.* 89, 10721–10725.

Morrow, J. D., Awad, J. A., Wu, A., Zackert, W. E., Daniel, V. C., and Roberts, L. J., II (1996) *J. Biol. Chem.* 271, 23185–23190.

Morrow, J. D., Harris, T. M., and Roberts, L. J., II (1990) *Anal. Biochem.* 184, 1–10.

Morrow, J. D., Hill, K. E., Burk, R. F., Nammour, T. M., Badr, K. F., and Roberts, L. J., II A series of prostaglandin-like compounds produced in vivo in humans by a non-cyclooxygenase, free radical catalyzed mechanism. (1990) *Proc. Natl. Acad. Sci. U.S.A.* 87, 9383–9387.

Morrow, J. D., Minton, T. A., Mukundan, C. R., Campbell, M. D., Zackert, W. E., Daniel, V. C., Badr, K. F., Blair, I. A., and Roberts, L. J., II (1994) *J. Biol. Chem.* 269, 4317–4326. Pace-Acsiak, C. R. and Wolfe, L. S. (1971) *J. Chromatogr.* 56, 129–135.

Morrow, J. D., Prakash, C., Awad, J. A., Duckworth, T A., Zakert, W. E., Blair, I. A., Oates, J. A., and Roberts, L. J., II (1991) *Anal. Bioichem* 193, 142–148

Narumiya, S., Ohno, K., Fujiwara, M., and Fukushima, M. (1986) *J. Pharmacol. Exp. Ther.* 239, 506–511.

Narumiya, S., Ohno, K., Fukushima, M., and Fujiwara, M. (1987) *J. Pharmacol. Exp. Ther.* 242, 306–311.

Pace-Asciak, C. R. (1989) *Adv. Prostaglandin Thromboxane Leukotriene Res.* 18, 322.

Ricote, M., Li, A. C., Willson, T. M., Kelly, C. J., and Glass, C. K. (1998) *Nature* 391, 79–82.

Roberts, L. J., II, and Morrow, J. D. (1997) *Biochim. Biophys. Acta.* 1345, 121–135.

Roberts L and Morrow J. Formation of novel isoprostane—like compounds for docosahexaenoic acid. R A Isma, R A Armstrong, R W Kelly, and R Wilson, Editors. Fourth International Congress on Essential Fatty Acids and Eicosanoids 1997; AOCS Press, Champaigne, Ill. In press.

Salem, N., Jr., and Niebylske, C. D. (1995) *Mol. Membr. Biol.* 12, 131–134.

Salem, N., Jr., Kim, H. -Y., and Yergery, J. A. (1986) *Health Effects of Polyunsaturated Fatty Acids in Seafoods* (Simopoulos, A. P., Kifer, R. R., and Martin, R. E., eds) pp. 263–317, Academic Press, Orlando, Fla.

Santoro, M. G. (1997) *Trends Microbiol.* 5, 276–281.

Saunders, A M, Strittmatter W J, Schmechel D, St. George-Hyslop PH, M. A P-V, Joo S H, Rosi B L, Gusella J F, Crapper M D, Alberts M J, Hulette C, Crain B, Goldgaber D, and Roses A D. Association of apolipoprotein E allele epsilon 4 with late-onset familial and sporadic Alzheimer's disease. Neurology 1993; 43(8):1467–72.

Shahabi, N. A., Chegini, N., and Wittliff, J. L. (1987) *Exp. Cell Biol.* 55, 18–27.

Simonian N. A., and Coyle, J. T. (1996) *Annu. Rev. Pharmacol. Toxicol.* 36, 83–106.

Skinner, E. R., Watt, C., Besson, J. A. O., and Best, P. V. (1993) *Brain* 116, 717–725.

Strittmatter W J and Roses A D. Apolipoprotein E and Alzheimer's disease. Proc Natl Acad Sci 1995; 92:4725–4727.

Taber, D. F., Morrow, J. D., and Roberts, L. J., II (1997) *Prostaglandins* 53, 63–67.

Tokugawa, Y., Kunishige, I., Kubota, Y., Shimoya, K., Nobunaga, T., Kimura, T., Saji, F., Murata, Y., Eguchi, N., Oda, H., Urade, Y., and Hayaishi, O. (1998) *Biol Reprod.* 58, 600–607

What is claimed is:

1. A marker for oxidative stress comprising isolated and purified neuroprostanes, which increase in a biological sample compared to a control sample during oxidative stress.

2. The marker according to claim 1, wherein said neuroprostanes is $F_2$-neuroprostane.

3. The marker according to claim 1, wherein said neuroprostanes is $E_2$-neuroprostane.

4. The marker according to claim 1, wherein said neuroprostanes is $D_2$-neuroprostane.

5. An isolated and purified neuroprostane formed by a process selected from the group consisting of beta oxidation, omega oxidation double bond reduction, dehydrogenation of side chain hydroxyl groups and reduction of a ring carbonyl to a hydroxyl group.

* * * * *